United States Patent [19]

Larsen

[11] Patent Number: 5,418,158

[45] Date of Patent: * May 23, 1995

[54] DNA SEQUENCES ENCODING NOVEL THROMBOLYTIC PROTEINS

[75] Inventor: Glenn Larsen, Sudbury, Mass.

[73] Assignee: Genetics Institute, Inc., Cambridge, Mass.

[*] Notice: The portion of the term of this patent subsequent to Dec. 10, 2008 has been disclaimed.

[21] Appl. No.: 103,938

[22] Filed: Aug. 6, 1993

Related U.S. Application Data

[63] Continuation of Ser. No. 805,415, Dec. 10, 1991, Pat. No. 5,258,298, which is a continuation of Ser. No. 382,678, Oct. 19, 1988, Pat. No. 5,071,972, which is a continuation-in-part of Ser. No. 861,699, May 9, 1986, abandoned, and a continuation-in-part of Ser. No. 853,781, Apr. 18, 1986, abandoned, and a continuation-in-part of Ser. No. 825,104, Jan. 31, 1986, abandoned, and a continuation-in-part of Ser. No. 882,051, Jul. 3, 1986, Pat. No. 5,002,887.

[51] Int. Cl.$^6$ .............................................. C12N 15/58
[52] U.S. Cl. ..................................... 435/226; 536/23.2
[58] Field of Search ............... 435/212, 226; 536/23.2, 536/23.5

[56] References Cited

U.S. PATENT DOCUMENTS 4,766,075  8/1988  Goeddel ........................ 435/240.2
5,071,972 12/1991  Larsen ................................ 536/27

OTHER PUBLICATIONS van Zonneveld, A. J. et al., *PNAS*, 83: 4670–4674, 1986.

*Primary Examiner*—Garnette D. Draper
*Assistant Examiner*—Marianne Porta Allen
*Attorney, Agent, or Firm*—Steven R. Lazar; Thomas J. DesRosier

[57] ABSTRACT

Thrombolytic proteins are disclosed which have tissue plasminogen-type activity. The proteins are characterized by modification within the 94 amino acid N-terminus, and/or at Arg-275, and/or at one or more of the N-linked glycosylation sites. Methods for making these proteins are disclosed as are therapeutic compositions containing same.

2 Claims, 32 Drawing Sheets

FIGURE 1

| REGION | FROM | TO |
| --- | --- | --- |
| 1 | Gly -(-3) | Gln-3 |
| 2 | Val-4 | Lys-10 |
| 3 | Thr-11 | His-18 |
| 4 | Gln-19 | Leu-22 |
| 5 | Arg-23 | Arg-27 |
| 6 | Ser-28 | Tyr-33 |
| 7 | Cys-34 | Cys-43 |
| 8 | His-44 | Ser-50 |
| 9 | Cys-51 | Cys-62 |
| 10 | Gln-63 | Val-72 |
| 11 | Cys-73 | Cys-84 |
| 12 | Glu-85 | Thr-91 |

FIGURE 2

|      | R¹           |      |      | R²          |      |      | R³           |      |      |
|------|------|------|------|------|------|------|------|------|------|
| (wt) | (Asn | Ser  | Ser) | (Asn | Gly  | Ser) | (Asn | Arg  | Thr) |
| I    | U    | Ser  | Ser  | V    | Gly  | Ser  | V    | Arg  | Thr  |
| II   | Asn  | W    | Ser  | Asn  | X    | Ser  | Asn  | Y    | Thr  |
| III  | Asn  | Ser  | Z    | Asn  | Gly  | Z    | Asn  | Arg  | U    |
| IV   | Asn  | W    | Z    | Asn  | X    | Z    | Asn  | Y    | U    |
| V    | −    | U    | *    | −    | *    | −    | −    | *    | −    |
| VI   | −    | Asn  | *    | −    | *    | *    | −    | *    | *    |
| VII  | U    | *    | *    | −    | −    | *    | −    | −    | *    |
| VIII | Asn  | *    | −    | *    | *    | −    | *    | *    | −    |
| IX   | −    | −    | −    | −    | −    | −    | −    | −    | −    |

```
−  = a peptide bond
*  = any amino acid
U  = any amino acid except Asn, Thr or Ser
V  =     "       "     "     "    Asn, or a peptide bond
W  =     "       "     "     "    Ser, or a peptide bond
X  =     "       "     "     "    Gly, or a peptide bond
Y  =     "       "     "     "    Arg, or a peptide bond
Z  =     "       "     "     "    Thr or ser, or a peptide bond
wt =  wild type, i.e., prior to mutagenesis
```

FIGURE 3

```
 -3    GARSYQVICR DEKTQMIYQQ HQSWLRPVLR SNRVEYCWCN SGRAQCHSVP
 48    VKSCSEPRCF NGGTCQQALY FSDFVCQCPE GFAGKCCEID TRATCYEDQG
 98    ISYRGTWSTA ESGAECTNW- R¹ALAQKPYS GRRPDAIRLG LGNHNYCRNP
148    DRDSKPWCYV FKAGKYSSEF CSTPACSEGN SDCYFG-R²A YRGTHSLTES
198    GASCLPWNSM ILIGKVYTAQ NPSAQALGLG KHNYCRNPDG DAKPWCHVLK
248    NRTLTWEYCD VPSCSTCGLR QYSQPQFJIK GGLFADIASH PWQAAIFAKH
298    RRSPGERFLC GGILISSCWI LSAAHCFQER FPPHHLTVIL GRTYRVVPGE
348    EEQKFEVEKY IVHKEFDDDT YDNDIALLQL KSDSSRCAQE SSVVRTVCLP
398    PADLQLPDWT ECELSGYGKH EALSPFYSER LKEAHVRLYP SSRCTSQHLL
448    -R³VTDNMLC AGDTRSGGPQ ANLHDACQGD SGGPLVCLND GRMTLVGIIS
498    WGLGCGQKDV PGVYTKVTNY LDWIRDNMRP
```

| compound | R¹ | R² | R³ | compound | R¹ | R² | R³ |
|---|---|---|---|---|---|---|---|
| wt | NSS | NGS | NRT | | | | |
| 1-1 | QSS | NGS | NRT | 1-12 | NSA | NGS | NRT |
| 1-2 | NSS | QGS | NRT | 1-13 | NSS | NGA | NRT |
| 1-3 | NSS | NGS | QRT | 1-14 | NSS | NGS | NRA |
| 1-4 | QSS | QGS | NRT | 1-15 | NSA | NGA | NRT |
| 1-5 | QSS | NGS | -RT | 1-16 | NSA | NGS | NRA |
| 1-6 | NSS | -GS | QRT | 1-17 | NSV | NGS | NRA |
| 1-7 | QSS | -GS | -RT | 1-18 | NSS | NGV | NRV |
| 1-8 | --- | --- | - | 1-19 | TSS | NGS | NRT |
| 1-9 | N-Q | N-S | N-T | 1-20 | TSS | TGS | NRT |
| 1-10 | N-- | N-- | N-- | 1-21 | TSS | TGS | QRT |
| 1-11 | --Q | --S | --T | | | | |

J = other than Arg, preferably other than Arg or Lys
R¹, R², and R³ are independently selected from the group consisting of a peptide bond, amino acid, dipeptide or tripeptide, and at least one of R¹, R² and R³ are other than consensus N-linked glycosylation sequences; "-", "--" and "---" = a peptide bond.

FIGURE 4

| compound | N-terminal sequence | | | | |
|---|---|---|---|---|---|
| D-1 | | | | | |
| | GARSYQVIC- | ---------- | ---------- | ---------- | ---------- |
| | ----CSEPRCF | NGGTCQQALY | FSDFVCQCPE | GFAGKCCEID | TRAT |
| D-2 | | | | | |
| | GARSYQ---- | ---------- | ---------- | ---------- | ---------- |
| | ----SEPRCF | NGGTCQQALY | FSDFVCQCPE | GFAGKCCEID | TRAT |
| D-3 | | | | | |
| | GARSYQVI-- | ---------- | ---------- | ---------- | ---------- |
| | ---------- | ---------- | ---------- | --------D | TRAT |
| D-4 | | | | | |
| | ---------- | ---------- | ---------- | ---------- | ---------- |
| | ---------- | ---------- | ---------- | --------D | TRAT |
| D-5 | | | | | |
| | ---------- | ---------- | ---------- | ---------- | ---------- |
| | ---------- | ---------- | ---------- | ---------- | ---- |
| D-6 | | | | | |
| | GARSYQVICR | DEKTQMIYQQ | HQSWLRPVLR | SNRVEYCWCN | SGRAQCHSVP |
| | VKS------- | ---------- | ---------- | ---------- | TRAT |

"-" indicates site of an amino acid deletion

FIGURE 5A

| compound | J | R¹ | R² | R³ | amino terminus |
|---|---|---|---|---|---|
| (wt) | R | NSS | NGS | NRT | G-(-3) thru T-91 |
| 2-0 | R | NSS | NGS | NRT | * |
| 2-1 | R | QSS | NGS | NRT | * |
| 2-2 | R | NSS | QGS | NRT | * |
| 2-3 | R | NSS | NGS | QRT | * |
| 2-4 | R | NSS | QGS | QRT | * |
| 2-5 | R | QSS | NGS | QRT | * |
| 2-6 | R | QSS | QGS | NRT | * |
| 2-7 | R | QSS | QGS | QRT | * |
| 2-8 | R | QSS | NGS | -RT | * |
| 2-9 | R | NSS | -GS | QRT | * |
| 2-10 | R | QSS | -GS | -RT | * |
| 2-11 | R | - | - | - | * |
| 2-12 | - | wt | wt | wt | * |
| 2-13 | G | wt | wt | wt | * |
| 2-14 | A | wt | wt | wt | * |
| 2-15 | T | wt | wt | wt | * |
| 2-16 | # | QSS | NGS | NRT | * |
| 2-17 | # | NSS | QGS | NRT | * |
| 2-18 | # | NSS | NGS | QRT | * |
| 2-19 | # | NSS | QGS | QRT | * |
| 2-20 | # | QSS | NGS | QRT | * |
| 2-21 | # | QSS | QGS | NRT | * |
| 2-22 | # | QSS | QGS | QRT | * |
| 2-23 | # | QSS | NGS | -RT | * |
| 2-24 | # | NSS | -GS | QRT | * |
| 2-25 | # | QSS | -GS | -RT | * |
| 2-26 | # | - | - | - | * |

| compound | J | R¹ | | | R² | R³ | N-terminus |
|---|---|---|---|---|---|---|---|
| 2-27 | R | U | Ser | Ser | wt | wt | * |
| 2-28 | # | U | Ser | Ser | wt | wt | * |
| 2-29 | R | Asn | W | Ser | wt | wt | * |
| 2-30 | # | Asn | W | Ser | wt | wt | * |
| 2-31 | R | Asn | Ser | Z | wt | wt | * |
| 2-32 | # | Asn | Ser | Z | wt | wt | * |
| 2-33 | R | Asn | W | Z | wt | wt | * |
| 2-34 | # | Asn | W | Z | wt | wt | * |
| 2-35 | R | - | U | ^ | wt | wt | * |
| 2-36 | # | - | U | ^ | wt | wt | * |
| 2-37 | R | - | Asn | ^ | wt | wt | * |
| 2-38 | # | - | Asn | ^ | wt | wt | * |
| 2-39 | R | U | ^ | ^ | wt | wt | * |
| 2-40 | # | U | ^ | ^ | wt | wt | * |
| 2-41 | R | Asn | ^ | - | wt | wt | * |
| 2-42 | # | Asn | ^ | - | wt | wt | * |
| 2-43 | R | | - | | wt | wt | * |
| 2-44 | # | | - | | wt | wt | * |

* indicates a N-terminus which is different at at least one amino acid relative to the wt N-terminus, illustrative examples of which are depicted below in FIGURE 6 and in FIGURES 7-10, & 12 ; "#" represents a peptide bond or an amino acid other than Arginine (R); "-" represents a peptide bond; U is any amino acid except Asn, Thr or Ser; W is a peptide bond or any amino acid except Ser; Z is a peptide bond or any amino acid except Thr or Ser; ^ is any amino acid; and wt indicates wild type.

FIGURE 6A

```
N- terminus
Designation

1    GARSYQVICR DEKTQM---- ---WLRPVLR SNRVEYCWCN SGRAQCHSVP
     VKSCSEPRCF NGGTCQQALY FSDFVCQCPE GFAGKCCEID TRAT

2    GARSYQVICR DEKTQMIYQQ HQSWLRPVLR SNRVEYCWCN SG-------P
     VKSCSEPRCF NGGTCQQALY FSDFVCQCPE GFAGKCCEID TRAT

3    GAR------- ---------- ---------- -NRVEYCWCN SGRAQCHSVP
     VKSCSEPRCF NGGTCQQALY FSDFVCQCPE GFAGKCCEID TRAT

4    GAR------- ---------- ---------- ---VEYCWCN SGRAQCHSVP
     VKSCSEPRCF NGGTCQQALY FSDFVCQCPE GFAGKCCEID TRAT

5    GAR------- ---------- ---------- ----EYCWCN SGRAQCHSVP
     VKSCSEPRCF NGGTCQQALY FSDFVCQCPE GFAGKCCEID TRAT

6    GARSYQVICR DEKTQMIYQQ HQSWLRPVLR SNRVEYCW-- ------HSVP
     VKSCSEPRCF NGGTCQQALY FSDFVCQCPE GFAGKCCEID TRAT

7    GARSYQVICR DEKTQMIYQQ HQSWLRPVLR SNRVEYCWC- ------HSVP
     VKSCSEPRCF NGGTCQQALY FSDFVCQCPE GFAGKCCEID TRAT

8    GARSYQVICR DEKTQMIYQQ HQSWLRPVLR SNRVEYCWC- -GRAQCHSVP
     VKSCSEPRCF NGGTCQQALY FSDFVCQCPE GFAGKCCEID TRAT

9    GARSYQVICR DEKTQMIYQQ HQSWLRPVLR SNRVEYCWCN --RAQCHSVP
     VKSCSEPRCF NGGTCQQALY FSDFVCQCPE GFAGKCCEID TRAT

10   GARSYQVICR DEKTQMIYQQ HQSWLRPVLR SNRVEYCWCN SGRAQCHSVP
     VKS------- ----CQQALY FSDFVCQCPE GFAGKCCEID TRAT

11   GARSYQVICR DEKTQMIYQQ HQSWLRPVLR SNRVEYCWCN SGRAQCHSVP
     VKSCSEPRCF NGGTCQQALY FSDFVC---- -------EID TRAT

12   GARSYQVIC- ---------- ---------- ----------N SGRAQCHSVP
     VKSCSEPRCF NGGTCQQALY FSDFVCQCPE GFAGKCCEID TRAT

13   GARSYQVI-- ---------- ---------- ---------- ----------
     ------PRCF NGGTCQQALY FSDFVCQCPE GFAGKCCEID TRAT

14   GARSYQVICR DEK------- ---------- ---VEYCWCN SGRAQCHSVP
     VKSCSEPRCF NGGTCQQALY FSDFVCQCPE GFAGKCCEID TRAT
```

FIGURE 6B

```
15  GARSYQVICR DEKTQMIYQQ H--------- ------CWCN SGRAQCHSVP
    VKSCSEPRCF NGGTCQQALY FSDFVCQCPE GFAGKCCEID TRAT

16  GARSYQVICR DEKTQMIYQQ HQSWLRPVLR SNRVEYCWCN SGRAQ----
    ---CSEPRCF NGGTCQQALY FSDFVCQCPE GFAGKCCEID TRAT

17  GARSYQVICR DEKTQMIYQQ HQSWLRPVLR SNRVEYCWCN SGRAQCHSVP
    VKSCSEPRC- ---------- ------QCPE GFAGKCCEID TRAT

18  GARSYQVICR DEKTQMIYQQ HQSWLRPVLR SNRVEYCWCN SGRAQCHSVP
    VKSC------ ---------- --------PE GFAGKCCEID TRAT

19  GARSYQVICR DEKTQMIYQQ HQSWLRPVLR SNRVEYCWCN SGRAQCHSVP
    VKSCSEPRC- ---------- ----VCQCPE GFAGKCCEID TRAT

20  GARSYQVICR DEKTQMIYQQ HQSWLRPVLR SNRVEYCWCN SGRAQCHSVP
    VKS------- ---------- ------QCPE GFAGKCCEID TRAT

21  GARSYQVIC- ---------- ---------- ---------- ----------
    ----SEPRCF NGGTCQQALY FSDFVCQCPE GFAGKCCEID TRAT

22  GARSYQVI-- ---------- ---------- ---------- ----------
    ---------- ---------- ---------- --------D TRAT

23  GARSYQVICR DEKTQMIYQQ HQSWLRPVLR SNRVEYCWCN SGRAQCHSVP
    VKS------- ---------- ---------- ---------- TRAT

424 GARSYQVICR DEKTQMIYQQ HQSWLRPVLR SNRVEYCWCN SGRAQCHSV-
    ---CSEPRCF NGGTCQQALY FSDFVCQCPE GFAGKCCEID TRAT

425 GARSYQVICR DEKTQMIYQQ HQSWLRPV-R SNR-EYCWCN SGRAQCHSVP
    VKSCSEPRCF NGGTCQQALY FSDFVCQCPE GFAGKCCEID TRAT

426 GARSYQVICR DEKTQMIYQQ HQSWLRP--R SNR--YCWCN SGRAQCHSVP
    VKSCSEPRCF NGGTCQQALY FSDFVCQCPE GFAGKCCEID TRAT

427 GARSYQVICR DEKTQMIYQ- HQSWLRPV-R SNR-EYCWCN SGRAQCHSVP
    VKSCSEPRCF NGGTCQQALY FSDFVCQCPE GFAGKCCEID TRAT

428 GARSYQVICR DEKTQMI--Q HQSWLRP--R SNR--YCWCN SGRAQCHSVP
    VKSCSEPRCF NGGTCQQALY FSDFVCQCPE GFAGKCCEID TRAT
```

Specific proteins of this invention may be referred to by a 3-part designation comprising a compound number from Figure 5 followed by a designation of N-terminus and then identification of positon 275. For example, compound No. 2-11/N-6/Arg designates a protein wherein the 3 glycosylation sites are deleted ("2-11", See Figure 5), C-36 through C-43 are deleted (N-terminus #N-6) and Arg-275 is retained.

FIGURE 7A

N-Terminus
Designation

24   GAR-YQVICR DEKTQMIYQQ HQSWLRPVLR SNRVEYCWCN SGRAQCHSVP
     VKSCSEPRCF NGGTCQQALY FSDFVCQCPE GFAGKCCEID TRAT

25   GARS-QVICR DEKTQMIYQQ HQSWLRPVLR SNRVEYCWCN SGRAQCHSVP
     VKSCSEPRCF NGGTCQQALY FSDFVCQCPE GFAGKCCEID TRAT

26   GARSY-VICR DEKTQMIYQQ HQSWLRPVLR SNRVEYCWCN SGRAQCHSVP
     VKSCSEPRCF NGGTCQQALY FSDFVCQCPE GFAGKCCEID TRAT

27   GARSYQ-ICR DEKTQMIYQQ HQSWLRPVLR SNRVEYCWCN SGRAQCHSVP
     VKSCSEPRCF NGGTCQQALY FSDFVCQCPE GFAGKCCEID TRAT

28   GARSYQV-CR DEKTQMIYQQ HQSWLRPVLR SNRVEYCWCN SGRAQCHSVP
     VKSCSEPRCF NGGTCQQALY FSDFVCQCPE GFAGKCCEID TRAT

29   GARSYQVI-R DEKTQMIYQQ HQSWLRPVLR SNRVEYCWCN SGRAQCHSVP
     VKSCSEPRCF NGGTCQQALY FSDFVCQCPE GFAGKCCEID TRAT

30   GARSYQVIC- DEKTQMIYQQ HQSWLRPVLR SNRVEYCWCN SGRAQCHSVP
     VKSCSEPRCF NGGTCQQALY FSDFVCQCPE GFAGKCCEID TRAT

31   GARSYQVICR -EKTQMIYQQ HQSWLRPVLR SNRVEYCWCN SGRAQCHSVP
     VKSCSEPRCF NGGTCQQALY FSDFVCQCPE GFAGKCCEID TRAT

32   GARSYQVICR D-KTQMIYQQ HQSWLRPVLR SNRVEYCWCN SGRAQCHSVP
     VKSCSEPRCF NGGTCQQALY FSDFVCQCPE GFAGKCCEID TRAT

33   GARSYQVICR DE-TQMIYQQ HQSWLRPVLR SNRVEYCWCN SGRAQCHSVP
     VKSCSEPRCF NGGTCQQALY FSDFVCQCPE GFAGKCCEID TRAT

34   GARSYQVICR DEK-QMIYQQ HQSWLRPVLR SNRVEYCWCN SGRAQCHSVP
     VKSCSEPRCF NGGTCQQALY FSDFVCQCPE GFAGKCCEID TRAT

35   GARSYQVICR DEKT-MIYQQ HQSWLRPVLR SNRVEYCWCN SGRAQCHSVP
     VKSCSEPRCF NGGTCQQALY FSDFVCQCPE GFAGKCCEID TRAT

36   GARSYQVICR DEKTQ-IYQQ HQSWLRPVLR SNRVEYCWCN SGRAQCHSVP
     VKSCSEPRCF NGGTCQQALY FSDFVCQCPE GFAGKCCEID TRAT

37   GARSYQVICR DEKTQM-YQQ HQSWLRPVLR SNRVEYCWCN SGRAQCHSVP
     VKSCSEPRCF NGGTCQQALY FSDFVCQCPE GFAGKCCEID TRAT

38   GARSYQVICR DEKTQMI-QQ HQSWLRPVLR SNRVEYCWCN SGRAQCHSVP
     VKSCSEPRCF NGGTCQQALY FSDFVCQCPE GFAGKCCEID TRAT

FIGURE 7B

N-Terminus
Designation

| | | | | | |
|---|---|---|---|---|---|
| 39 | GARSYQVICR | DEKTQMIY-Q | HQSWLRPVLR | SNRVEYCWCN | SGRAQCHSVP |
| | VKSCSEPRCF | NGGTCQQALY | FSDFVCQCPE | GFAGKCCEID | TRAT |
| 40 | GARSYQVICR | DEKTQMIYQ- | HQSWLRPVLR | SNRVEYCWCN | SGRAQCHSVP |
| | VKSCSEPRCF | NGGTCQQALY | FSDFVCQCPE | GFAGKCCEID | TRAT |
| 41 | GARSYQVICR | DEKTQMIYQQ | -QSWLRPVLR | SNRVEYCWCN | SGRAQCHSVP |
| | VKSCSEPRCF | NGGTCQQALY | FSDFVCQCPE | GFAGKCCEID | TRAT |
| 42 | GARSYQVICR | DEKTQMIYQQ | H-SWLRPVLR | SNRVEYCWCN | SGRAQCHSVP |
| | VKSCSEPRCF | NGGTCQQALY | FSDFVCQCPE | GFAGKCCEID | TRAT |
| 43 | GARSYQVICR | DEKTQMIYQQ | HQ-WLRPVLR | SNRVEYCWCN | SGRAQCHSVP |
| | VKSCSEPRCF | NGGTCQQALY | FSDFVCQCPE | GFAGKCCEID | TRAT |
| 44 | GARSYQVICR | DEKTQMIYQQ | HQS-LRPVLR | SNRVEYCWCN | SGRAQCHSVP |
| | VKSCSEPRCF | NGGTCQQALY | FSDFVCQCPE | GFAGKCCEID | TRAT |
| 45 | GARSYQVICR | DEKTQMIYQQ | HQSW-RPVLR | SNRVEYCWCN | SGRAQCHSVP |
| | VKSCSEPRCF | NGGTCQQALY | FSDFVCQCPE | GFAGKCCEID | TRAT |
| 46 | GARSYQVICR | DEKTQMIYQQ | HQSWL-PVLR | SNRVEYCWCN | SGRAQCHSVP |
| | VKSCSEPRCF | NGGTCQQALY | FSDFVCQCPE | GFAGKCCEID | TRAT |
| 47 | GARSYQVICR | DEKTQMIYQQ | HQSWLR-VLR | SNRVEYCWCN | SGRAQCHSVP |
| | VKSCSEPRCF | NGGTCQQALY | FSDFVCQCPE | GFAGKCCEID | TRAT |
| 48 | GARSYQVICR | DEKTQMIYQQ | HQSWLRP-LR | SNRVEYCWCN | SGRAQCHSVP |
| | VKSCSEPRCF | NGGTCQQALY | FSDFVCQCPE | GFAGKCCEID | TRAT |
| 49 | GARSYQVICR | DEKTQMIYQQ | HQSWLRPV-R | SNRVEYCWCN | SGRAQCHSVP |
| | VKSCSEPRCF | NGGTCQQALY | FSDFVCQCPE | GFAGKCCEID | TRAT |
| 50 | GARSYQVICR | DEKTQMIYQQ | HQSWLRPVL- | SNRVEYCWCN | SGRAQCHSVP |
| | VKSCSEPRCF | NGGTCQQALY | FSDFVCQCPE | GFAGKCCEID | TRAT |
| 51 | GARSYQVICR | DEKTQMIYQQ | HQSWLRPVLR | -NRVEYCWCN | SGRAQCHSVP |
| | VKSCSEPRCF | NGGTCQQALY | FSDFVCQCPE | GFAGKCCEID | TRAT |
| 52 | GARSYQVICR | DEKTQMIYQQ | HQSWLRPVLR | S-RVEYCWCN | SGRAQCHSVP |
| | VKSCSEPRCF | NGGTCQQALY | FSDFVCQCPE | GFAGKCCEID | TRAT |
| 53 | GARSYQVICR | DEKTQMIYQQ | HQSWLRPVLR | SN-VEYCWCN | SGRAQCHSVP |
| | VKSCSEPRCF | NGGTCQQALY | FSDFVCQCPE | GFAGKCCEID | TRAT |

FIGURE 7C

N-Terminus
Designation

| | | | | | |
|---|---|---|---|---|---|
| 54 | GARSYQVICR | DEKTQMIYQQ | HQSWLRPVLR | SNR-EYCWCN | SGRAQCHSVP |
| | VKSCSEPRCF | NGGTCQQALY | FSDFVCQCPE | GFAGKCCEID | TRAT |
| 55 | GARSYQVICR | DEKTQMIYQQ | HQSWLRPVLR | SNRV-YCWCN | SGRAQCHSVP |
| | VKSCSEPRCF | NGGTCQQALY | FSDFVCQCPE | GFAGKCCEID | TRAT |
| 56 | GARSYQVICR | DEKTQMIYQQ | HQSWLRPVLR | SNRVE-CWCN | SGRAQCHSVP |
| | VKSCSEPRCF | NGGTCQQALY | FSDFVCQCPE | GFAGKCCEID | TRAT |
| 57 | GARSYQVICR | DEKTQMIYQQ | HQSWLRPVLR | SNRVEY-WCN | SGRAQCHSVP |
| | VKSCSEPRCF | NGGTCQQALY | FSDFVCQCPE | GFAGKCCEID | TRAT |
| 58 | GARSYQVICR | DEKTQMIYQQ | HQSWLRPVLR | SNRVEYC-CN | SGRAQCHSVP |
| | VKSCSEPRCF | NGGTCQQALY | FSDFVCQCPE | GFAGKCCEID | TRAT |
| 59 | GARSYQVICR | DEKTQMIYQQ | HQSWLRPVLR | SNRVEYCW-N | SGRAQCHSVP |
| | VKSCSEPRCF | NGGTCQQALY | FSDFVCQCPE | GFAGKCCEID | TRAT |
| 60 | GARSYQVICR | DEKTQMIYQQ | HQSWLRPVLR | SNRVEYCWC- | SGRAQCHSVP |
| | VKSCSEPRCF | NGGTCQQALY | FSDFVCQCPE | GFAGKCCEID | TRAT |
| 61 | GARSYQVICR | DEKTQMIYQQ | HQSWLRPVLR | SNRVEYCWCN | -GRAQCHSVP |
| | VKSCSEPRCF | NGGTCQQALY | FSDFVCQCPE | GFAGKCCEID | TRAT |
| 62 | GARSYQVICR | DEKTQMIYQQ | HQSWLRPVLR | SNRVEYCWCN | S-RAQCHSVP |
| | VKSCSEPRCF | NGGTCQQALY | FSDFVCQCPE | GFAGKCCEID | TRAT |
| 63 | GARSYQVICR | DEKTQMIYQQ | HQSWLRPVLR | SNRVEYCWCN | SG-AQCHSVP |
| | VKSCSEPRCF | NGGTCQQALY | FSDFVCQCPE | GFAGKCCEID | TRAT |
| 64 | GARSYQVICR | DEKTQMIYQQ | HQSWLRPVLR | SNRVEYCWCN | SGR-QCHSVP |
| | VKSCSEPRCF | NGGTCQQALY | FSDFVCQCPE | GFAGKCCEID | TRAT |
| 65 | GARSYQVICR | DEKTQMIYQQ | HQSWLRPVLR | SNRVEYCWCN | SGRA-CHSVP |
| | VKSCSEPRCF | NGGTCQQALY | FSDFVCQCPE | GFAGKCCEID | TRAT |
| 66 | GARSYQVICR | DEKTQMIYQQ | HQSWLRPVLR | SNRVEYCWCN | SGRAQ-HSVP |
| | VKSCSEPRCF | NGGTCQQALY | FSDFVCQCPE | GFAGKCCEID | TRAT |
| 67 | GARSYQVICR | DEKTQMIYQQ | HQSWLRPVLR | SNRVEYCWCN | SGRAQC-SVP |
| | VKSCSEPRCF | NGGTCQQALY | FSDFVCQCPE | GFAGKCCEID | TRAT |
| 68 | GARSYQVICR | DEKTQMIYQQ | HQSWLRPVLR | SNRVEYCWCN | SGRAQCH-VP |
| | VKSCSEPRCF | NGGTCQQALY | FSDFVCQCPE | GFAGKCCEID | TRAT |

FIGURE 7D

N-Terminus
Designation
↓

69  GARSYQVICR DEKTQMIYQQ HQSWLRPVLR SNRVEYCWCN SGRAQCHS-P
    VKSCSEPRCF NGGTCQQALY FSDFVCQCPE GFAGKCCEID TRAT

70  GARSYQVICR DEKTQMIYQQ HQSWLRPVLR SNRVEYCWCN SGRAQCHSV-
    VKSCSEPRCF NGGTCQQALY FSDFVCQCPE GFAGKCCEID TRAT

71  GARSYQVICR DEKTQMIYQQ HQSWLRPVLR SNRVEYCWCN SGRAQCHSVP
    -KSCSEPRCF NGGTCQQALY FSDFVCQCPE GFAGKCCEID TRAT

72  GARSYQVICR DEKTQMIYQQ HQSWLRPVLR SNRVEYCWCN SGRAQCHSVP
    V-SCSEPRCF NGGTCQQALY FSDFVCQCPE GFAGKCCEID TRAT

73  GARSYQVICR DEKTQMIYQQ HQSWLRPVLR SNRVEYCWCN SGRAQCHSVP
    VK-CSEPRCF NGGTCQQALY FSDFVCQCPE GFAGKCCEID TRAT

74  GARSYQVICR DEKTQMIYQQ HQSWLRPVLR SNRVEYCWCN SGRAQCHSVP
    VKS-SEPRCF NGGTCQQALY FSDFVCQCPE GFAGKCCEID TRAT

FIGURE 8A

N-terminus
Designation

| | | | | | |
|---|---|---|---|---|---|
| 75 | GARSYQVICR | DEKTQMIYQQ | HQSWLRPVLR | SNRVEYCWCN | SGRAQCHSVP |
| | VKS------- | ---------- | ---------- | ---------- | TRAT |
| 10 | GARSYQVICR | DEKTQMIYQQ | HQSWLRPVLR | SNRVEYCWCN | SGRAQCHSVP |
| | VKS------- | ----CQQALY | FSDFVCQCPE | GFAGKCCEID | TRAT |
| 11 | GARSYQVICR | DEKTQMIYQQ | HQSWLRPVLR | SNRVEYCWCN | SGRAQCHSVP |
| | VKSCSEPRCF | NGGTCQQALY | FSDFVC---- | -------EID | TRAT |
| 17 | GARSYQVICR | DEKTQMIYQQ | HQSWLRPVLR | SNRVEYCWCN | SGRAQCHSVP |
| | VKSCSEPRC- | ---------- | ------QCPE | GFAGKCCEID | TRAT |
| 18 | GARSYQVICR | DEKTQMIYQQ | HQSWLRPVLR | SNRVEYCWCN | SGRAQCHSVP |
| | VKSC------ | ---------- | --------PE | GFAGKCCEID | TRAT |
| 19 | GARSYQVICR | DEKTQMIYQQ | HQSWLRPVLR | SNRVEYCWCN | SGRAQCHSVP |
| | VKSCSEPRC- | ---------- | ----VCQCPE | GFAGKCCEID | TRAT |
| 20 | GARSYQVICR | DEKTQMIYQQ | HQSWLRPVLR | SNRVEYCWCN | SGRAQCHSVP |
| | VKS------- | ---------- | ------QCPE | GFAGKCCEID | TRAT |
| 21 | GARSYQVIC- | ---------- | ---------- | ---------- | ---------- |
| | ----SEPRCF | NGGTCQQALY | FSDFVCQCPE | GFAGKCCEID | TRAT |
| 22 | GARSYQVI-- | ---------- | ---------- | ---------- | ---------- |
| | ---------- | ---------- | ---------- | ---------D | TRAT |
| 23 | GARSYQVICR | DEKTQMIYQQ | HQSWLRPVLR | SNRVEYCWCN | SGRAQCHSVP |
| | VKS------- | ---------- | ---------- | ---------- | TRAT |
| 76 | GARSYQVI-- | ---------- | --SWLRPVLR | SN-------- | -----CHSVP |
| | VK-------- | -----QQALY | FSDFVCQCPE | GFAGKCCEID | TRAT |
| 74 | GARSYQVICR | DEKTQMIYQQ | HQSWLRPVLR | SNRVEYCWCN | SGRAQCHSVP |
| | VKS-SEPRCF | NGGTCQQALY | FSDFVCQCPE | GFAGKCCEID | TRAT |
| 77 | GARSYQVICR | DEKTQMIYQQ | HQSWLRPVLR | SNRVEYCWCN | SGRAQCHSVP |
| | VKSC-EPRCF | NGGTCQQALY | FSDFVCQCPE | GFAGKCCEID | TRAT |
| 78 | GARSYQVICR | DEKTQMIYQQ | HQSWLRPVLR | SNRVEYCWCN | SGRAQCHSVP |
| | VKSCS-PRCF | NGGTCQQALY | FSDFVCQCPE | GFAGKCCEID | TRAT |
| 79 | GARSYQVICR | DEKTQMIYQQ | HQSWLRPVLR | SNRVEYCWCN | SGRAQCHSVP |
| | VKSCSE-RCF | NGGTCQQALY | FSDFVCQCPE | GFAGKCCEID | TRAT |
| 80 | GARSYQVICR | DEKTQMIYQQ | HQSWLRPVLR | SNRVEYCWCN | SGRAQCHSVP |
| | VKSCSEP-CF | NGGTCQQALY | FSDFVCQCPE | GFAGKCCEID | TRAT |

FIGURE 8B

<u>N-terminus</u>
<u>Designation</u>
<u>#</u>

81     GARSYQVICR DEKTQMIYQQ HQSWLRPVLR SNRVEYCWCN SGRAQCHSVP
         VKSCSEPR-F NGGTCQQALY FSDFVCQCPE GFAGKCCEID TRAT

82     GARSYQVICR DEKTQMIYQQ HQSWLRPVLR SNRVEYCWCN SGRAQCHSVP
         VKSCSEPRC- NGGTCQQALY FSDFVCQCPE GFAGKCCEID TRAT

83     GARSYQVICR DEKTQMIYQQ HQSWLRPVLR SNRVEYCWCN SGRAQCHSVP
         VKSCSEPRCF -GGTCQQALY FSDFVCQCPE GFAGKCCEID TRAT

84     GARSYQVICR DEKTQMIYQQ HQSWLRPVLR SNRVEYCWCN SGRAQCHSVP
         VKSCSEPRCF N-GTCQQALY FSDFVCQCPE GFAGKCCEID TRAT

85     GARSYQVICR DEKTQMIYQQ HQSWLRPVLR SNRVEYCWCN SGRAQCHSVP
         VKSCSEPRCF NG-TCQQALY FSDFVCQCPE GFAGKCCEID TRAT

86     GARSYQVICR DEKTQMIYQQ HQSWLRPVLR SNRVEYCWCN SGRAQCHSVP
         VKSCSEPRCF NGG-CQQALY FSDFVCQCPE GFAGKCCEID TRAT

87     GARSYQVICR DEKTQMIYQQ HQSWLRPVLR SNRVEYCWCN SGRAQCHSVP
         VKSCSEPRCF NGGT-QQALY FSDFVCQCPE GFAGKCCEID TRAT

88     GARSYQVICR DEKTQMIYQQ HQSWLRPVLR SNRVEYCWCN SGRAQCHSVP
         VKSCSEPRCF NGGTC-QALY FSDFVCQCPE GFAGKCCEID TRAT

89     GARSYQVICR DEKTQMIYQQ HQSWLRPVLR SNRVEYCWCN SGRAQCHSVP
         VKSCSEPRCF NGGTCQ-ALY FSDFVCQCPE GFAGKCCEID TRAT

90     GARSYQVICR DEKTQMIYQQ HQSWLRPVLR SNRVEYCWCN SGRAQCHSVP
         VKSCSEPRCF NGGTCQQ-LY FSDFVCQCPE GFAGKCCEID TRAT

91     GARSYQVICR DEKTQMIYQQ HQSWLRPVLR SNRVEYCWCN SGRAQCHSVP
         VKSCSEPRCF NGGTCQQA-Y FSDFVCQCPE GFAGKCCEID TRAT

92     GARSYQVICR DEKTQMIYQQ HQSWLRPVLR SNRVEYCWCN SGRAQCHSVP
         VKSCSEPRCF NGGTCQQAL- FSDFVCQCPE GFAGKCCEID TRAT

93     GARSYQVICR DEKTQMIYQQ HQSWLRPVLR SNRVEYCWCN SGRAQCHSVP
         VKSCSEPRCF NGGTCQQALY -SDFVCQCPE GFAGKCCEID TRAT

94     GARSYQVICR DEKTQMIYQQ HQSWLRPVLR SNRVEYCWCN SGRAQCHSVP
         VKSCSEPRCF NGGTCQQALY F-DFVCQCPE GFAGKCCEID TRAT

95     GARSYQVICR DEKTQMIYQQ HQSWLRPVLR SNRVEYCWCN SGRAQCHSVP
         VKSCSEPRCF NGGTCQQALY FS-FVCQCPE GFAGKCCEID TRAT

96     GARSYQVICR DEKTQMIYQQ HQSWLRPVLR SNRVEYCWCN SGRAQCHSVP
         VKSCSEPRCF NGGTCQQALY FSD-VCQCPE GFAGKCCEID TRAT

FIGURE 8C

N-terminus
Designation

97  GARSYQVICR DEKTQMIYQQ HQSWLRPVLR SNRVEYCWCN SGRAQCHSVP
    VKSCSEPRCF NGGTCQQALY FSDF-CQCPE GFAGKCCEID TRAT

98  GARSYQVICR DEKTQMIYQQ HQSWLRPVLR SNRVEYCWCN SGRAQCHSVP
    VKSCSEPRCF NGGTCQQALY FSDFV-QCPE GFAGKCCEID TRAT

99  GARSYQVICR DEKTQMIYQQ HQSWLRPVLR SNRVEYCWCN SGRAQCHSVP
    VKSCSEPRCF NGGTCQQALY FSDFVC-CPE GFAGKCCEID TRAT

100 GARSYQVICR DEKTQMIYQQ HQSWLRPVLR SNRVEYCWCN SGRAQCHSVP
    VKSCSEPRCF NGGTCQQALY FSDFVCQ-PE GFAGKCCEID TRAT

101 GARSYQVICR DEKTQMIYQQ HQSWLRPVLR SNRVEYCWCN SGRAQCHSVP
    VKSCSEPRCF NGGTCQQALY FSDFVCQCP- GFAGKCCEID TRAT

102 GARSYQVICR DEKTQMIYQQ HQSWLRPVLR SNRVEYCWCN SGRAQCHSVP
    VKSCSEPRCF NGGTCQQALY FSDFVCQCPE -FAGKCCEID TRAT

103 GARSYQVICR DEKTQMIYQQ HQSWLRPVLR SNRVEYCWCN SGRAQCHSVP
    VKSCSEPRCF NGGTCQQALY FSDFVCQCPE G-AGKCCEID TRAT

104 GARSYQVICR DEKTQMIYQQ HQSWLRPVLR SNRVEYCWCN SGRAQCHSVP
    VKSCSEPRCF NGGTCQQALY FSDFVCQCPE GF-GKCCEID TRAT

105 GARSYQVICR DEKTQMIYQQ HQSWLRPVLR SNRVEYCWCN SGRAQCHSVP
    VKSCSEPRCF NGGTCQQALY FSDFVCQCPE GFA-KCCEID TRAT

106 GARSYQVICR DEKTQMIYQQ HQSWLRPVLR SNRVEYCWCN SGRAQCHSVP
    VKSCSEPRCF NGGTCQQALY FSDFVCQCPE GFAG-CCEID TRAT

107 GARSYQVICR DEKTQMIYQQ HQSWLRPVLR SNRVEYCWCN SGRAQCHSVP
    VKSCSEPRCF NGGTCQQALY FSDFVCQCPE GFAGK-CEID TRAT

108 GARSYQVICR DEKTQMIYQQ HQSWLRPVLR SNRVEYCWCN SGRAQCHSVP
    VKSCSEPRCF NGGTCQQALY FSDFVCQCPE GFAGKC-EID TRAT

109 GARSYQVICR DEKTQMIYQQ HQSWLRPVLR SNRVEYCWCN SGRAQCHSVP
    VKSCSEPRCF NGGTCQQALY FSDFVCQCPE GFAGKCC-ID TRAT

110 GARSYQVICR DEKTQMIYQQ HQSWLRPVLR SNRVEYCWCN SGRAQCHSVP
    VKSCSEPRCF NGGTCQQALY FSDFVCQCPE GFAGKCCE-D TRAT

111 GARSYQVICR DEKTQMIYQQ HQSWLRPVLR SNRVEYCWCN SGRAQCHSVP
    VKSCSEPRCF NGGTCQQALY FSDFVCQCPE GFAGKCCEI- TRAT

FIGURE 8D

N-terminus
Designation
↨

312   GARSYQVICR DEKTQMIYQQ HQSWLRPVLR SNRVEYCWCN SGRAQCHSVP
      VKSCSEPRCF NGGTCQQAL- ---DFVCQCPE GFAGKCCEID TRAT

313   GARSYQVICR DEKTQMIYQQ HQSWLRPVLR SNRVEYCWCN SGRAQCHSVP
      VKSCSEPRCF NGGTCQQALY --DFVCQCPE GFAGKCCEID TRAT

314   GARSYQVICR DEKTQMIYQQ HQSWLRPVLR SNRVEYCWCN SGRAQCHSVP
      VKSCSEPRCF NGGTCQQAL- -SDFVCQCPE GFAGKCCEID TRAT

315   GARSYQVI-- ---------- ---------- ---------- ----------
      ---CSEPRCF NGGTCQQAL- FSDFVCQCPE GFAGKCCEID TRAT

316   GARSYQVI-- ---------- ---------- ---------- ----------
      ---CSEPRCF NGGTCQQALY -SDFVCQCPE GFAGKCCEID TRAT

317   GARSYQVI-- ---------- ---------- ---------- ----------
      ---CSEPRCF NGGTCQQALY F-DFVCQCPE GFAGKCCEID TRAT

318   GARSYQVI-- ---------- ---------- ---------- ----------
      ---CSEPRCF NGGTCQQALY --DFVCQCPE GFAGKCCEID TRAT

319   GARSYQVI-- ---------- ---------- ---------- ----------
      ---CSEPRCF NGGTCQQAL- --DFVCQCPE GFAGKCCEID TRAT

FIGURE 9A

Compound Designation
2-26/N-75/-
2-26/N-74Δ6/-
2-27/N-74Δ1, N-76Δ6/-

Deletions
C-51 through D-87
C-51 through C-56
C-51, E-53 through N-58

FIGURE 9B

Compound Designation

2-0/N-424/Arg
2-0/N-425/Arg
2-0/N-426/Arg
2-0/N-427/Arg
2-0/N-428/Arg
2-0/N-63Δ2,N-92Δ3/Arg
2-0/N-63Δ1,N-92Δ2/Arg
2-0/N-63Δ1,N-92Δ1/Arg

Modification: Deletion of:

P-47 through S-50
L-26 & V-31
V-25, L-26, V-31 & E-32
Q-17, L-26, & V-31
Y-15, Q-16, V-25, L-26, V-31 & E-32
R-40, A-41, Y-67, F-68 & S-69
R-40, Y-67 & F-68
R-40 & Y-67

FIGURE 9C

```
2-1/N-424/Arg
2-1/N-425/Arg
2-1/N-426/Arg
2-1/N-427/Arg
2-1/N-428/Arg
2-1/N-63Δ2, N-92Δ3/Arg
2-1/N-63Δ1, N-92Δ2/Arg
2-1/N-63Δ1, N-92Δ1/Arg
```

FIGURE 9D

```
2-7/N-424/Arg
2-7/N-425/Arg
2-7/N-426/Arg
2-7/N-427/Arg
2-7/N-428/Arg
2-7/N-63Δ2, N-92Δ3/Arg
2-7/N-63Δ1, N-92Δ2/Arg
2-7/N-63Δ1, N-92Δ1/Arg
```

FIGURE 10

<u>N-terminus</u>
<u>Designation</u>

112 GARSYQVICR ---------- -QSWLRPVLR SNRVEYCWCN SGRAQCHSVP
    VKSCSEPRCF NGGTCQQALY FSDFVCQCPE GFAGKCCEID TRAT

113 GARSYQVICR DEKTQMIYQQ HQSWLRPVLR ---------- -GRAQCHSVP
    VKSCSEPRCF NGGTCQQALY FSDFVCQCPE GFAGKCCEID TRAT

114 GARSYQVICR DEKTQMIYQQ HQSWLRPVLR SNRVEYCWCN SGRAQCHSVP
    VKS------- ----CQQALY FSDFVCQCPE GFAGKCCEID TRAT

115 GARSYQVICR DEKTQMIYQQ HQSWLRPVLR SNRVEYCWCN SGRAQCHSVP
    VKSCSEPRCF NGGTCQQALY FSDF------ -----CCEID TRAT

116 GARSYQVICR ---------- HQSWLRPVLR SNRVEYCWCN SGRAQCHSVP
    VKS------- -GGTCQQALY FSDFVCQCPE GFAGKCCEID TRAT

117 GARSYQVICR ---------- HQSWLRPVLR ---------- SGRAQCHSVP
    VKSCSEPRCF NGGTCQQALY FSDFVCQCPE GFAGKCCEID TRAT

118 GARSYQVICR ---------- HQSWLRPVLR SNRVEYCWCN SGRAQCHSVP
    VKSCSEPRCF NGGTCQQALY FSDFV----- -----CCEID TRAT

119 GARSYQVICR DEKTQMIYQQ HQSWLRPVLR ---------- SGRAQCHSVP
    VKSCSEPRCF NGGTCQQALY FSD------- ---GKCCEID TRAT

120 GARSYQVICR DEKTQMIYQQ HQSWLRPVLR ---------- SGRAQCHSVP
    VKSCS----- ----CQQALY FSDFVCQCPE GFAGKCCEID TRAT

121 GARSYQVICR DEKTQMIYQQ HQSWLRPVLR SNRVEYCWCN SGRAQCHSVP
    VKSCS----- -GGTCQQALY FSDFV----- -----CCEID TRAT

And, with reference to Figure 6, 7, and 8:

N-1
N-2
N-6         through   N-11
N-15        through   N-17
N-24Δ1 through Δ19
N-27Δ1 through Δ19
N-44Δ1 through Δ19
N-73Δ1 through Δ19
N-95Δ1 through Δ19
N111Δ1 through Δ5

FIGURE 11

| wt | --> | replacement | wt | --> | replacement |
|---|---|---|---|---|---|
| C-6 | | S,T,G or A | | | |
| R-7 | | S,T,Q,N,G,H,D or K | S-52 | | G,A,Q,L,V,I or |
| D-8 | | " " | E-53 | | S,T,Q,N,G,H,D O |
| E-9 | | " " | P-54 | | A,G,Y,D or S |
| K-10 | | " " | R-55 | | S,T,Q,N,G,H,D orK |
| T-11 | | N,S,L,G or A | C-56 | | S, T, G or A |
| Q-12 | | N,S,L,G,A or T | F-57 | | Y,I,W,H,D or R |
| | | | N-58 | | G,A,Q,L,V,I or T |
| M-13 | | " " | G-59 | | A,S,T,D,V or P |
| I-14 | | " " | G-60 | | " " |
| Q-16 | | " " | T-61 | | N,S,L,G or A |
| Q-17 | | " " | Q-63 | | N,S,L,G,A or T |
| H-18 | | " " | Q-64 | | " " |
| R-23 | | S,T,Q,N,G,H,D or K | A-65 | | G,S,T,H,N or Q |
| R-27 | | " " | L-66 | | N,S,L,G,A or T |
| R-30 | | " " | L-67 | | Y,I,W,H,D or R |
| V-31 | | " " | F-68 | | " " |
| E-32 | | S,T,Q,N,G,H,D or K | S-69 | | G,A,Q,L,V,I or T |
| Y-33 | | F,S,H or L | D-70 | | S,T,Q,N,G,H,D or K |
| W-35 | | T,V,I or Q | F-71 | | Y,I,W,H,D or R |
| N-37 | | G,A,Q,L,V,I or T | V-72 | | N,S,L,G,A or T |
| S-38 | | " " | Q-74 | | N,S,L,G or A |
| G-39 | | A,S,T,D,V or P | P-76 | | A,G,Y,D or S |
| R-40 | | S,T,N,G or D | E-77 | | S,T,Q,N,G,H,D or K |
| A-41 | | G,S,T,H,N or Q | G-78 | | A,S,T,D,V or P |
| Q-42 | | N,S,L,G,A or T | F-79 | | Y,I,W,H,D or R |
| H-44 | | " " | A-80 | | G,S,T,H,N or Q |
| S-45 | | G,A,Q,L,V,I or T | G-81 | | A,S,T,D,V or P |
| V-46 | | N,S,L,G,A orT | K-82 | | S,T,Q,N,G,H,D or K |
| P-47 | | A,G,Y,D or S | C-83 | | S or T |
| V-48 | | N,J,L,G,A or T | C-84 | | S or T |
| K-49 | | S,T,Q,N,G,H,D orK | E-85 | | S,T,Q,N,G,H,D or K |
| S-50 | | G,A,Q,L,V,I orT | I-86 | | N,S,L,G,A or T |
| C-51 | | S, T, G or A | D-87 | | S,T,Q,N,G,H,D or K |
| | | | T-88 | | N,S,L,G or A |
| | | | R-89 | | S,T,N,G or D |
| | | | A-90 | | G,S,T,H,N or Q |
| | | | T-91 | | N,S,L,G or A |

FIGURE 12A

N-Terminus
Designation

| | | | | | |
|---|---|---|---|---|---|
| 122 | GAR<u>G</u>YQVICR | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 123 | GARS<u>F</u>QVICR | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 124 | GARSY<u>N</u>VICR | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 125 | GARSYQ<u>J</u>ICR | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 126 | GARSYQV<u>S</u>CR | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 127 | GARSYQVI<u>S</u>R | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 128 | GARSYQVIC<u>T</u> | DEKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 129 | GARSYQVICR | <u>N</u>EKTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 130 | GARSYQVICR | D<u>Q</u>KTQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 131 | GARSYQVICR | DE<u>T</u>TQMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 132 | GARSYQVICR | DEK<u>A</u>QMIYQQ | HQSWLRPVLR | SNRVEYCWCN | SGRAQCHSVP |
| | VKSCSEPRCF | NGGTCQQALY | FSDFVCQCPE | GFAGKCCEID | TRAT |
| 133 | GARSYQVICR | DEKT<u>L</u>MIYQQ | HQSWLRPVLR | SNRVEYCWCN | SGRAQCHSVP |
| | VKSCSEPRCF | NGGTCQQALY | FSDFVCQCPE | GFAGKCCEID | TRAT |

FIGURE 12B

```
134    GARSYQVICR DEKTQGIYQQ HQSWLRPVLR SNRVEYCWCN SGRAQCHSVP
       VKSCSEPRCF NGGTCQQALY FSDFVCQCPE GFAGKCCEID TRAT

135    GARSYQVICR DEKTQMAYQQ HQSWLRPVLR SNRVEYCWCN SGRAQCHSVP
       VKSCSEPRCF NGGTCQQALY FSDFVCQCPE GFAGKCCEID TRAT

136    GARSYQVICR DEKTQMISQQ HQSWLRPVLR SNRVEYCWCN SGRAQCHSVP
       VKSCSEPRCF NGGTCQQALY FSDFVCQCPE GFAGKCCEID TRAT

137    GARSYQVICR DEKTQMIYLQ HQSWLRPVLR SNRVEYCWCN SGRAQCHSVP
       VKSCSEPRCF NGGTCQQALY FSDFVCQCPE GFAGKCCEID TRAT

138    GARSYQVICR DEKTQMIYQL HQSWLRPVLR SNRVEYCWCN SGRAQCHSVP
       VKSCSEPRCF NGGTCQQALY FSDFVCQCPE GFAGKCCEID TRAT

139    GARSYQVICR DEKTQMIYQQ NQSWLRPVLR SNRVEYCWCN SGRAQCHSVP
       VKSCSEPRCF NGGTCQQALY FSDFVCQCPE GFAGKCCEID TRAT

140    GARSYQVICR DEKTQMIYQQ HDSWLRPVLR SNRVEYCWCN SGRAQCHSVP
       VKSCSEPRCF NGGTCQQALY FSDFVCQCPE GFAGKCCEID TRAT

141    GARSYQVICR DEKTQMIYQQ HQNWLRPVLR SNRVEYCWCN SGRAQCHSVP
       VKSCSEPRCF NGGTCQQALY FSDFVCQCPE GFAGKCCEID TRAT

142    GARSYQVICR DEKTQMIYQQ HQSYLRPVLR SNRVEYCWCN SGRAQCHSVP
       VKSCSEPRCF NGGTCQQALY FSDFVCQCPE GFAGKCCEID TRAT

143    GARSYQVICR DEKTQMIYQQ HQSWERPVLR SNRVEYCWCN SGRAQCHSVP
       VKSCSEPRCF NGGTCQQALY FSDFVCQCPE GFAGKCCEID TRAT

144    GARSYQVICR DEKTQMIYQQ HQSWLGPVLR SNRVEYCWCN SGRAQCHSVP
       VKSCSEPRCF NGGTCQQALY FSDFVCQCPE GFAGKCCEID TRAT

145    GARSYQVICR DEKTQMIYQQ HQSWLRTVLR SNRVEYCWCN SGRAQCHSVP
       VKSCSEPRCF NGGTCQQALY FSDFVCQCPE GFAGKCCEID TRAT

146    GARSYQVICR DEKTQMIYQQ HQSWLRPYLR SNRVEYCWCN SGRAQCHSVP
       VKSCSEPRCF NGGTCQQALY FSDFVCQCPE GFAGKCCEID TRAT

147    GARSYQVICR DEKTQMIYQQ HQSWLRPVDR SNRVEYCWCN SGRAQCHSVP
       VKSCSEPRCF NGGTCQQALY FSDFVCQCPE GFAGKCCEID TRAT

148    GARSYQVICR DEKTQMIYQQ HQSWLRPVLS SNRVEYCWCN SGRAQCHSVP
       VKSCSEPRCF NGGTCQQALY FSDFVCQCPE GFAGKCCEID TRAT

149    GARSYQVICR DEKTQMIYQQ HQSWLRPVLR PNRVEYCWCN SGRAQCHSVP
       VKSCSEPRCF NGGTCQQALY FSDFVCQCPE GFAGKCCEID TRAT

150    GARSYQVICR DEKTQMIYQQ HQSWLRPVLR SDRVEYCWCN SGRAQCHSVP
       VKSCSEPRCF NGGTCQQALY FSDFVCQCPE GFAGKCCEID TRAT
```

FIGURE 12C

151  GARSYQVICR DEKTQGIYQQ HQSWLRPVLR SNSVEYCWCN SGRAQCHSVP
     VKSCSEPRCF NGGTCQQALY FSDFVCQCPE GFAGKCCEID TRAT

152  GARSYQVICR DEKTQMIYQQ HQSWLRPVLR SNRLEYCWCN SGRAQCHSVP
     VKSCSEPRCF NGGTCQQALY FSDFVCQCPE GFAGKCCEID TRAT

153  GARSYQVICR DEKTQMIYQQ HQSWLRPVLR SNRVSYCWCN SGRAQCHSVP
     VKSCSEPRCF NGGTCQQALY FSDFVCQCPE GFAGKCCEID TRAT

154  GARSYQVICR DEKTQMIYQQ HQSWLRPVLR SNRVESCWCN SGRAQCHSVP
     VKSCSEPRCF NGGTCQQALY FSDFVCQCPE GFAGKCCEID TRAT

155  GARSYQVICR DEKTQMIYQQ HQSWLRPVLR SNRVEYSWCN SGRAQCHSVP
     VKSCSEPRCF NGGTCQQALY FSDFVCQCPE GFAGKCCEID TRAT

156  GARSYQVICR DEKTQMIYQQ HQSWLRPVLR SNRVEYCTCN SGRAQCHSVP
     VKSCSEPRCF NGGTCQQALY FSDFVCQCPE GFAGKCCEID TRAT

157  GARSYQVICR DEKTQMIYQQ HQSWLRPVLR SNRVEYCWTN SGRAQCHSVP
     VKSCSEPRCF NGGTCQQALY FSDFVCQCPE GFAGKCCEID TRAT

158  GARSYQVICR DEKTQMIYQQ HQSWLRPVLR SNRVEYCWCD SGRAQCHSVP
     VKSCSEPRCF NGGTCQQALY FSDFVCQCPE GFAGKCCEID TRAT

159  GARSYQVICR DEKTQMIYQQ HQSWLRPVLR SNRVEYCWCN PGRAQCHSVP
     VKSCSEPRCF NGGTCQQALY FSDFVCQCPE GFAGKCCEID TRAT

160  GARSYQVICR DEKTQMIYQQ HQSWLRPVLR SNRVEYCWCN SARAQCHSVP
     VKSCSEPRCF NGGTCQQALY FSDFVCQCPE GFAGKCCEID TRAT

161  GARSYQVICR DEKTQMIYQQ HQSWLRPVLR SNRVEYCWCN SGSAQCHSVP
     VKSCSEPRCF NGGTCQQALY FSDFVCQCPE GFAGKCCEID TRAT

162  GARSYQVICR DEKTQMIYQQ HQSWLRPVLR SNRVEYCWCN SGRVQCHSVP
     VKSCSEPRCF NGGTCQQALY FSDFVCQCPE GFAGKCCEID TRAT

163  GARSYQVICR DEKTQMIYQQ HQSWLRPVLR SNRVEYCWCN SGRALCHSVP
     VKSCSEPRCF NGGTCQQALY FSDFVCQCPE GFAGKCCEID TRAT

164  GARSYQVICR DEKTQMIYQQ HQSWLRPVLR SNRVEYCWCN SGRAQTHSVP
     VKSCSEPRCF NGGTCQQALY FSDFVCQCPE GFAGKCCEID TRAT

165  GARSYQVICR DEKTQMIYQQ HQSWLRPVLR SNRVEYCWCN SGRAQCSSVP
     VKSCSEPRCF NGGTCQQALY FSDFVCQCPE GFAGKCCEID TRAT

166  GARSYQVICR DEKTQMIYQQ HQSWLRPVLR SNRVEYCWCN SGRAQCHIVP
     VKSCSEPRCF NGGTCQQALY FSDFVCQCPE GFAGKCCEID TRAT

FIGURE 12D

```
167  GARSYQVICR DEKTQGIYQQ HQSWLRPVLR SNRVEYCWCN SGRAQCHSNP
     VKSCSEPRCF NGGTCQQALY FSDFVCQCPE GFAGKCCEID TRAT

168  GARSYQVICR DEKTQMIYQQ HQSWLRPVLR SNRVEYCWCN SGRAQCHSVD
     VKSCSEPRCF NGGTCQQALY FSDFVCQCPE GFAGKCCEID TRAT

169  GARSYQVICR DEKTQMIYQQ HQSWLRPVLR SNRVEYCWCN SGRAQCHSVP
     NKSCSEPRCF NGGTCQQALY FSDFVCQCPE GFAGKCCEID TRAT

170  GARSYQVICR DEKTQMIYQQ HQSWLRPVLR SNRVEYCWCN SGRAQCHSVP
     VDSCSEPRCF NGGTCQQALY FSDFVCQCPE GFAGKCCEID TRAT

171  GARSYQVICR DEKTQMIYQQ HQSWLRPVLR SNRVEYCWCN SGRAQCHSVP
     VKVCSEPRCF NGGTCQQALY FSDFVCQCPE GFAGKCCEID TRAT

172  GARSYQVICR DEKTQMIYQQ HQSWLRPVLR SNRVEYCWCN SGRAQCHSVP
     VTSCSEPRCF NGGTCQQALY FSDFVCQCPE GFAGKCCEID TRAT

173  GARSYQVICR DEKTQMIYQQ HQSWLRPVLR SNRVQYCWCN SGRAQCHSVP
     VKSCSEPRCF NGGTCQQALY FSDFVCQCPE GFAGKCCEID TRAT

174  GARSYQVICR NEKTQMIYQQ HQSWLRPVLR SNRVEYCWCN SGRAQCHSVP
     VKSCSEPRCF NGGTCQQALY FSDFVCQCPE GFAGKCCEID TRAT

175  GARSYQVICR DEKTQMIYQQ HQSWLRPVLR SNRVEYCWCN SGRAQCHSVP
     VKSCSEPRCF NGGTCQQAKY FSDFVCQCPE GFAGKCCEID TRAT

176  GARSYQVICR DEKTQMIYQQ HQSWLRPVLR SNRVEYCWCN SGRAQCHSVP
     VKSCSEPRCF NGGTCQQALA FSDFVCQCPE GFAGKCCEID TRAT

177  GARSYQVICR DEKTQMIYQQ HQSWLRPVLR SNRVEYCWCN SGRAQCHSVP
     VKSCSEPRCF NGGTCQQALG FSDFVCQCPE GFAGKCCEID TRAT

178  GARSYQVICR DEKTQMIYQQ HQSWLRPVLR SNRVEYCWCN SGRAQCHSVP
     VKSCSEPRCF NGGTCQQALY GSDFVCQCPE GFAGKCCEID TRAT

179  GARSYQVICR DEKTQMIYQQ HQSWLRPVLR SNRVEYCWCN SGRAQCHSVP
     VKSCSEPRCF NGGTCQQALY ASDFVCQCPE GFAGKCCEID TRAT

180  GARSYQVICR DEKTQMIYQQ HQSWLRPVLR SNRVEYCWCN SGRAQCHSVP
     VKSCSEPRCF NGGTCQQALY FSFFVCQCPE GFAGKCCEID TRAT

181  GARSYQVICR DEKTQMIYQQ HQSWLRPVLR SNRVEYCWCN SGRAQCHSVP
     VKSCSEGRCF NGGTCQQALY FSDFVCQCPE GFAGKCCEID TRAT

182  GARSYQVICR DEKTQMIYQQ HQSWLRPVLR SNRVEYCWCN SGRAQCHSVP
     VKSCSEPRCF NGGTCQQALY FSDFVCQCPE GFAGHCCEID TRAT

183  GARSYQVICR DEKTQMIYQQ HQSWLRPVLR SNRVEYCWCN SGRAQCHSVP
     VKSCSEPRCF NGGTCQQALY FSDFVCQCPE GFAGQCCEID TRAT

184  GARSYQVICR DEKTQGIYQQ HQSWLRPVLR SNRVEYCWCN SGRAQCHSVP
     VKSCSEPRCF NGGTCQQALY FSDFVCQCPE GFAGKCCEID TRAT
```

FIGURE 12E

185 GARSYQVICR DEKTQMIYQQ HQSWLRPVLR SNRVEYCWCN SGRAQCHSVP
    VKSCSEPRCF NGGTCQQALY FSDFVCQCP<u>T</u> GFAGKCCEID TRAT

186 GARSYQVICR DEKTQMIYQQ HQSWLRPVLR SNRVEYCWCN SGRAQCHSVP
    VKSCSEPRCF NGGTCQQALY FSDFVCQCPE GFAGKCCEI<u>H</u> TRAT

187 GARSYQVICR DEKTQMIYQQ HQSWLRPVLR SNRVEYCWCN SGRAQCHSVP
    VKSCSEP<u>T</u>CF NGGTCQQALY FSDFVCQCPE GFAGKCCEID TRAT

188 GARSYQVICR DEKTQMIYQQ HQSWLRPVLR SNRVEYCWCN SGRAQCHSVP
    VKSCSEPRCF NGGTCQQALY FS<u>S</u>FVCQCPE GFAGKCCEID TRAT

189 GARSYQVICR DEKTQMIYQQ HQSWLRPVLR SNRVEYCWCN SGRAQCHSVP
    VKSCSEP<u>H</u>CF NGGTCQQALY FSDFVCQCPE GFAGKCCEID TRAT

190 GARSYQVICR DEKTQMIYQQ HQSWLRPVLR SNRVEYCWCN SGRAQCHSVP
    VKSCSEPRCF <u>V</u>GGTCQQALY FSDFVCQCPE GFAGKCCEID TRAT

191 GARSYQVICR DEKTQMIYQQ HQSWLRPVLR SNRVEYCWCN SGRAQCHSVP
    VKSCS<u>T</u>PRCF NGGTCQQALY FSDFVCQCPE GFAGKCCEID TRAT

192 GARSYQVICR DEKTQMIYQQ HQSWLRPVLR SNRVEYCWCN SGRAQCHSVP
    VKSCS<u>Q</u>PRCF NGGTCQQALY FSDFVCQCPE GFAGKCCEID TRAT

193 GARSYQVICR DEKTQMIYQQ HQSWLRPVLR SNRVEYCWCN SGRAQCHSVP
    V<u>H</u>SCSEPRCF NGGTCQQALY FSDFVCQCPE GFAGKCCEID TRAT

194 GARSYQVICR DEKTQMIYQQ HQSWLRPVLR SNRVEYCWCN SGRAQCHSVP
    VKSCSEPRCF NGGTCQQALY <u>H</u>SDFVCQCPE GFAGKCCEID TRAT

195 GARSYQVICR DEKTQMIYQQ HQSWLRPVLR SNRVEYCWCN SGRAQCHSVP
    VKSCSEPRCF NGGTCQQALY <u>I</u>SDFVCQCPE GFAGKCCEID TRAT

196 GARSYQVICR DEKTQMIYQQ HQSWLRPVLR SNRVEYCWCN SGRAQCHSVP
    VKSCSEPRCF NGGTCQQALY <u>P</u>SDFVCQCPE GFAGKCCEID TRAT

197 GARSYQVICR DEKTQMIYQQ HQSWLRPVLR SNRVEYCWCN SGRAQCHSVP
    VKSCSEPRCF NGGTCQQALY <u>R</u>SDFVCQCPE GFAGKCCEID TRAT

198 GARSYQVICR DEKTQMIYQQ HQSWLRPVLR SNRVEYCWCN SGRAQCHSVP
    VKSCSEPRCF NGGTCQQALY F<u>I</u>DFVCQCPE GFAGKCCEID TRAT

199 GARSYQVICR DEKTQMIYQQ HQSWLRPVLR SNRVEYCWCN SGRA<u>L</u>CHSVP
    VKSCSEPRCF NGGTCQQALY FSDFVCQCPE GFAGKCCEID TRAT

200 GARSYQVICR DEKTQMIYQQ HQSWLRPVLR SNRVEYCWCN SGRAQCHSVP
    VKSCSEPRCF NGGTCQQ<u>E</u>LY FSDFVCQCPE GFAGKCCEID TRAT

201 GARSYQVICR DEKTQMIYQQ HQSWLRPVLR SNRVEYCWCN SGRAQCHSVP
    VKSCSEPRCF NGGTCQQA<u>N</u>Y FSDFVCQCPE GFAGKCCEID TRAT

202 GARSYQVICR DEKTQMIYQQ HQSWLRPVLR SNRVEYCWCN SGRAQCHSVP
    VKSCSEP<u>S</u>CF NGGTCQQALY FSDFVCQCPE GFAGKCCEID TRAT

FIGURE 13A

| Compound # | Substitutions: Wt | Replacement |
|---|---|---|
| 2-16/N-128, N-130/Thr | R-7<br>E-9 | T<br>Q |
| 2-16/N-129, N-130/Thr | D-8<br>E-9 | N<br>Q |
| 2-16/N-130, N-131/Thr | E-9<br>K-10 | Q<br>T |
| 2-16/N-131, N-153/Thr | K-10<br>E-32 | T<br>S |
| 2-16/N-161, N-165/Thr | R-40<br>H-44 | S<br>S |
| 2-16/N-159, N-161/Thr | S-38<br>R-40 | P<br>S |
| 2-16/N-161, N-163/Thr | R-40<br>Q-42 | S<br>L |
| 2-16/N-161, N-172/Thr | R-40<br>K-49 | S<br>T |
| 2-16/N-138, N-142/Thr | Q-17<br>W-21 | L<br>Y |
| 2-16/N-133, N-138/Thr | Q-12<br>Q-17 | L<br>L |
| 2-16/N-128, N-133/Thr | R-7<br>Q-12 | T<br>L |
| 2-16/N-131, N-162/Thr | K-10<br>A-41 | T<br>V |
| 2-16/N-165, N-170/Thr | H-44<br>K-49 | S<br>D |
| 2-16/N-143, N-146/Thr | L-22<br>V-25 | E<br>Y |
| 2-16/N-173, N-165/Thr | E-32<br>H-44 | Q<br>S |
| 2-16/N-165, N-172/Thr | H-44<br>K-49 | S<br>T |

FIGURE 13B

| | | |
|---|---|---|
| 2-16/N-148, N-151/Thr | R-27 | S |
| | R-30 | S |
| 2-16/N-143, N-153/Thr | L-22 | E |
| | E-32 | S |
| 2-16/N-161, N-170/Thr | R-40 | S |
| | K-49 | D |
| 2-16/N-153, N-161/Thr | E-32 | S |
| | R-40 | S |
| 2-16/N-129, N-131/Thr | D-8 | N |
| | K-10 | T |
| 2-16/N-131, N-143/Thr | K-10 | T |
| | L-22 | E |
| 2-16/N-128, N-131/Thr | R-7 | T |
| | K-10 | T |
| 2-16/N-128, N-161/Thr | S-7 | T |
| | R-40 | S |
| 2-16/N-175, N-176/Thr | L-66 | K |
| | Y-67 | A |
| 2-16/N-176, N-178/Thr | Y-67 | A |
| | F-68 | G |
| 2-16/N-177, N-170/Thr | Y-67 | G |
| | D-70 | F |
| 2-16/N-177, N-179/Thr | Y-67 | G |
| | F-68 | A |
| 2-16/N-181, N-182/Thr | P-54 | G |
| | K-82 | H |
| 2-16/N-202, N-183/Thr | R-55 | S |
| | K-82 | Q |
| 2-16/N-185, N-184/Thr | E-77 | T |
| | K-82 | N |
| 2-16/N-184, N-186/Thr | K-82 | N |
| | D-87 | H |

FIGURE 13C

| | | |
|---|---|---|
| 2-16/N-187, N-186/Thr | R-55 | T |
| | D-87 | H |
| 2-16/N-188, N-201/Thr | L-66 | N |
| | D-70 | S |
| 2-16/N-189, N-190/Thr | R-55 | H |
| | N-58 | V |
| 2-16/N-191, N-189/Thr | E-53 | T |
| | R-55 | H |
| 2-16/N-193, N-192/Thr | K-49 | H |
| | E-53 | Q |
| 2-16/N-161, N-175/Thr | R-40 | S |
| | L-66 | K |
| 2-16/N-148, N-194/Thr | R-27 | S |
| | F-68 | H |
| 2-16/N-131, N-184/Thr | K-10 | T |
| | F-68 | H |
| 2-16/N-174, N-195/Thr | D-8 | N |
| | F-68 | I |
| 2-16/N-144, N-195/Thr | R-23 | G |
| | F-68 | I |
| 2-16/N-151, N-196/Thr | R-30 | S |
| | F-68 | P |
| 2-16/N-161, N-198/Thr | R-40 | S |
| | S-69 | I |
| 2-16/N-199, N-200/Thr | Q-42 | L |
| | A-65 | E |
| 2-16/N-161, N-197/Thr | R-40 | S |
| | F-68 | R |

FIGURE 14

| No. | Sequence | Mutation |
|---|---|---|
| 1. | ACC AAC TGG <u>ACC</u> AGC AGC GCG | $Asn_{117} \longrightarrow Thr$ |
| 2. | CTAC TTT GGG <u>ACT</u> GGG TCA GC | $Asn_{184} \longrightarrow Thr$ |
| 3. | GTGCACCAACTGG<u>CA</u>GAGCAGCGCGTTGGC | $Asn_{117} \longrightarrow Gln$ |
| 4. | CAACTGG<u>CA</u>GAGCAGCG | (#3)* |
| 5. | ACTGCTACTTTGGG<u>CA</u>GGGGTCAGCCTACC | $Asn_{184} \longrightarrow Gln$ |
| 6. | CTTTGGG<u>CA</u>GGGGTCAG | (#5)* |
| 7. | CATTTACTT<u>CA</u>GAGAACAGTC | $Asn_{448} \longrightarrow Gln$ |
| 8. | GGA GCC AGA TCT TAC CAA GTG ATC TGC▲AGC GAG CCA AGG TGT TTC AAC GGG GGC | (Δ FBR) |
| 9. | TGATC TGC▲AGC GAG CC | (#8)* |
| 10. | A AGA GGA GCC AGA TCT TAC CAA GTG ATC▲GAT ACC AGG GCC ACG TGC TAC GAG | (ΔFBR/EGF) |
| 11. | CAA GTG ATC▲GAT ACC AG | (#10)* |
| 12. | TCA GTG CCT GTC AAA AGT▲ACC AGG GCC ACG TGC TAC | (Δ EGF) |
| 13. | GTC AAA AGT▲ACC AGG G | (#12)* |
| 14. | GC CAG CCT CAG TTT▲ATC AAA GGA GGG C | (R-275 del) |
| 15. | CT CAG TTT <u>ACC</u> ATC AAA G | ( $\longrightarrow$ T-275) |

*Used for screening the mutation indicated in parenthesis (where a screening oligonucleotide is not indicated, the same oligonucleotide is used for mutagenesis and screening).
Codons for replacment amino acids are underlined, ▲ indicates site of deletion. As those skilled in this art will appreciate, oligonucleotides can be readily constructed for use in deleting one or more amino acids or inserting a different (i.e., replacement) amino acid at a desired site by deleting the codon(s) or substituting the codon for the desired replacement amino acid, respectively, in the oligonucleotide. Other mutagenesis oligonucleotides can be designed based on an approximately 20-50 nucleotide sequence spanning the desired site, with replacement or deletion of the original codon(s) one wishes to change.

FIGURE 15

(I)
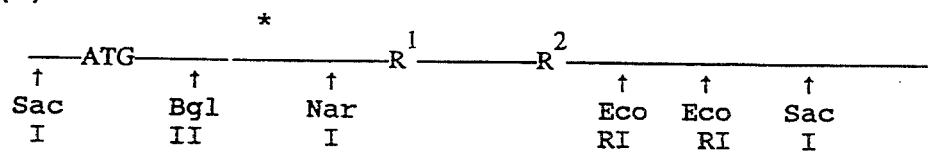

(II)
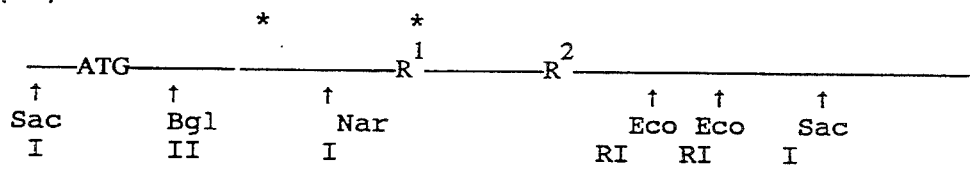

(III)
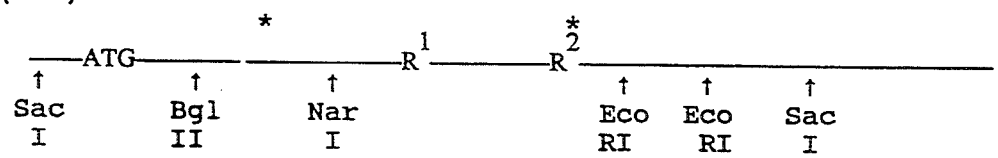

(IV)
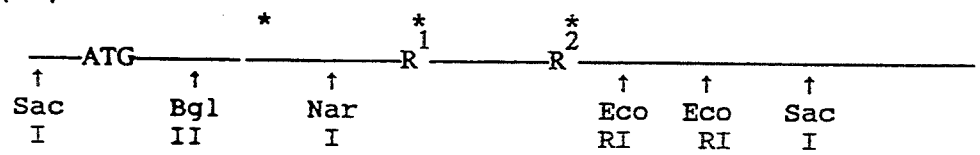

(V)
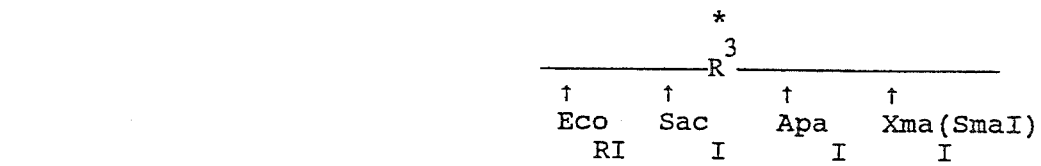

\* indicates site of mutagenesis; cDNA fragments I through IV are prepared by digesting pWGSM or pSVPA4 with SacI, inserting SacI fragment into M13 vector, mutagenizing with desired oligonucleotide(s), and digesting mutagenized M13/t-PA DNA with SacI; alternatively, I-IV may be excised from mutagenized M13/t-PA with BglII and SacI and the BglII/SacI fragment encoding the peptide domain spanning the N-terminus, $R^1$, $R^2$ & Arg-275 may be inserted into BglII/SacI-digested pIVPA; cDNA fragment V is prepared as described in Example 2, below.

FIGURE 16A

| Compound | Route | |
|---|---|---|
| D-6,<br>D-1<br>D-3 | (a) | ligate mutagenized cDNA fragment I (prepared using oligonucleotides #8,10 or 12) into SacI-digested pSVPA4, or excise fragment I from mutagenizedM13/t-PA as the BglII/SacI fragment and insert same into BglII/SacI-digested pIVPA/1. |
| 2-1/N-23/Arg<br>2-1/N-21/Arg<br>2-1/N-22/Arg | (b) | ligate mutagenized cDNA fragment II (prepared using oligonucleotides #8,10 or 12) and then oligonucleotide #3) into SacI-digested pSVPA4, or excise fragment II from mutagenized M13/t-PA as the BglII/SacI fragment and insert same into BglII/SacI-digested pIVPA/1. |
| 2-2/N-23/Arg<br>2-2/N-21/Arg<br>2-2/N-22/Arg | (c) | ligate mutagenized cDNA fragment III (prepared using oligonucleotides #8,10 or 12 and oligonucleotide #5) into SacI-digested pSVPA4 or excise fragment III from mutagenized M13/t-PA as the BglII/SacI fragment and insert same into BglII/SacI-digested pIVPA/1. |
| 2-3/N-23/Arg<br>2-3/N-21/Arg<br>2-3/N-21/Arg | (d) | digest mutagenized pIVPA/1 or pSVPA4 produced by Route(a) with EcoRI (partial digest) and XmaI (SmaI) or ApaI (total digest) to remove wild type $R^3$ coding region, and ligate thereto mutagenized cDNA fragment V (prepared using oligonucleotide #7) as the EcoRI/ApaI or EcoRI/XmaI (SmaI) fragment. |
| 2-4/N-23/Arg<br>2-4/N-21/Arg<br>2-4/N-22/Arg | (e) | digest mutagenized pIVPA or pSVPA prepared as in Route (c) with EcoRI (partial digest) and XmaI (SmaI) or ApaI (total digest) to remove wild type $R^3$-coding region, and ligate thereto cDNA fragment V (prepared using oligonucleotide #7) as the EcoRI/ApaI or EcoRI/XmaI (SmaI) fragment. |
| 2-5/N-23/Arg<br>2-5/N-21/Arg<br>2-5/N-22/Arg | (f) | digest mutagenized pIVPA or pSVPA4 prepared by Route(b) with EcoRI (partial digest) and XmaI (SmaI) or ApaI (total digest) and ligate thereto mutagenized cDNA fragment V (prepared using oligonucleotide #7) as the EcoRI/ApaI or EcoRI/XmaI (SmaI) fragment. |

FIGURE 16B 2-6/N-23/Arg  
2-6/N-21/Arg  
2-6/N-22/Arg (g) ligate mutagenized cDNA fragment IV (prepared using oligonucleotides #8,10 or 12 and oligonucleotides #3 and 5) into SacI-digested pSVPA4 or excise fragment IV from mutagenized M13/t-PA as the BglII/SacI fragment and ligate same into BglII/SacI-digested pIVPA/1.

2-7/N-23/Arg  
2-7/N-21/Arg  
2-7/N-22/Arg (h) ligate mutagenized cDNA fragment IV (prepared using oligonucleotides #8,10 or 12 and oligonucleotides #3 and 5) into SacI-digested pSVPA4 prepared by Routes (d), (e) or (f) or ligate fragment IV so produced as the BglII/SacI fragment into BglII/SacI-digested pIVPA produced by Route(s) (d), (e), of (f).

DNA SEQUENCES ENCODING NOVEL THROMBOLYTIC PROTEINS

This application is a continuation of application Ser. No. 07/805,415 filed Dec. 10, 1991, issued as U.S. Pat. No. 5,258,298, which is a continuation of Ser. No. 07/382,678 filed Oct. 19, 1988 issued as U.S. Pat. No. 5,071,972, which was based on PCT/US87/00267, filed on Jan. 30, 1987 and was a CIP of Ser. No. 06/861,699 filed May 9, 1986 presently abandoned; Ser. No. 06/853,781 filed Apr. 18, 1986 presently abandoned; Ser. No. 06/825,104 filed Jan. 31, 1986; presently abandoned; and Ser. No. 06/882,051 filed Jul. 3, 1986 issued as U.S. Pat. No. 5,002,887.

This invention relates to substances having tissue plasminogen activator-type (t-PA) activity. More specifically, this invention relates to "recombinant" thrombolytic proteins, a process for obtaining the proteins from genetically engineered cells, and the therapeutic use of the substances as thrombolytic agents.

These proteins are active thrombolytic agents which, it is contemplated, possess improved fibrinolytic profiles relative to native human t-PA. This may be manifested as increased affinity to fibrin, decreased reactivity with inhibitors of t-PA, faster rate of thrombolysis, increased fibrinolytic activity and/or prolonged biological half-life. It is also contemplated that proteins of this invention can be more conveniently prepared in more homogeneous form than can native human t-PA. An improved overall pharmacokinetic profile is contemplated for these proteins.

The structure of native human t-PA can be viewed as comprising an amino (N-) terminus of about 91 amino acid residues, two so-called "kringle" regions, and at the carboxy terminus a serine protease-type domain. We have found that the N-terminus contains several subdomains which play functional roles, inter alia, in fibrin binding and in the in vivo clearance of the protein. Recently the recovery of another form of t-PA which lacks the native N-terminus and first kringle region has been reported, see European Published Patent Application No. 0 196 920 (published 08 Oct. 1986). According to that report the truncated form of t-PA, which begins with Ala-160 of native human t-PA, is fibrinolytically active.

As described in greater detail hereinafter, this invention provides novel protein analogs of human t-PA which retain both kringle regions of native human t-PA, but contain modifications within the N-terminus. While in certain embodiments the modifications involve deletions in the N-terminus, the first kringle region is left intact, and the N-terminal deletion is never greater than 94 amino acids. Most embodiments involve significantly smaller deletion(s) and/or amino acid substitution(s). By retaining more of the structure of native human t-PA, it is contemplated that the proteins of this invention selectively retain more of the desirable biological activities of native human t-PA and may be less immunogenic than more drastically modified analogs of t-PA. It is therefore contemplated that the proteins of this invention possess improved fibrinolytic and pharmacokinetic profiles relative to both native human t-PA and the truncated Ala-160 t-PA, as well as other modified forms of t-PA.

The polypeptide backbone of natural human t-PA also includes four consensus Asn-linked glycosylation sites. It has been shown that two of these sites are typically glycosylated in t-PA from melanoma-derived mammalian cells, i.e. at $Asn_{117}$ and $Asn_{448}$. $Asn_{184}$ is glycosylated sometimes and $Asn_{218}$ is typically not glycosylated. t-PA from melanoma-derived mammalian cells, e.g. Bowes cells, is also referred to herein as "native" or "natural" human t-PA.

This invention, as mentioned above, involves novel protein analogs of human t-PA which possess t-PA-type thrombolytic activity. The proteins of this invention differ in structure from human t-PA in that they contain modifications in peptide sequence (i) at up to three of the Asn-linked glycosylation sites present in native t-PA; (ii) within the N-terminus of the proteins corresponding to the 94 amino acid mature N-terminus of native t-PA; and/or (iii) at the proteolytic cleavage site spanning Arg-275 and Ile-276. These features of the proteins of this invention are described in greater detail below. Notwithstanding the various modifications, the numbering of amino acids as shown in the one-letter code sequence of FIG. 3 is retained.

DESCRIPTION OF THE FIGURES

FIG. 1 shows the regions for amino acid deletions or substitutions within the present invention.

FIG. 2 shows exemplary modifications at N-linked glycosylation sites.

FIG. 3 shows illustrative proteins containing modification at Arg-275 and at least one N-linked glycosylation site.

FIG. 4 shows illustrative proteins having N-terminal deletions. The proteins have the peptide sequence shown in FIG. 3, wherein R1, R2 and R3 represent the wild-type tripeptide sequences, but wherein the N-termini (Gly-(-3) through Thr-91) are replaced with the sequences shown.

FIG. 5 shows illustrative proteins containing a deletion of 1 to 94 amino acids at the N-terminus and optional modification at either or both of Arg-275 and at least one N-linked glycosylation site. (For general sequence, see FIG. 3).

FIG. 6 shows illustrative N-termini containing a deletion of 1–94 amino acids. Specific proteins of this invention may be referred to by a 3-part designation comprising a compound number from FIG. 5, followed by a designation of N-terminus and then identification of position 275, for example, compound No. 2-11/N-6/Arg a protein wherein the 3 glycosylation sites are deleted ("2-11", see FIG. 5), C-36 through C-43 are deleted (N-terminus #N-6) and Arg-275 is retained.

FIGS. 7A–D shows exemplary proteins having a deletion of 1–45 amino acids in the region from Ser-1 through Ser-50 and a modification at either or both of Arg-275 and at least one N-linked glycosylation site. (For general sequence, see FIG. 3). Illustrative proteins are as defined in FIG. 5, but with the illustrated N-termini replacing the wild type (wt) sequence of Gly-(-3) through Thr-91.

FIGS. 8A–D show exemplary proteins having a deletion of 1–41 amino acids from the region Cys-51 through Thr-91. (For general sequence, see FIG. 3). Illustrative proteins are as defined in FIG. 5, but with the illustrated N-termini replacing the wild-type (wt) sequence of Gly-(-3) through Thr-91.

FIG. 9A shows examples of proteins wherein the three glycosylation sites and Arg-275 are deleted. FIG. 9B shows examples of proteins wherein no glycosylation sites are modified, but which contain various deletions. FIG. 9C shows compounds with deletions as above, which are also modified at the first N-linked glycosylation site, here by replacing Asn-117 with Gln. FIG. 9D shows compounds containing deletions as above, in which all three glycosylation sites are modified by replacement of Asn with Gln.

FIG. 10 shows exemplary proteins having one or more deletions of less than about 20 amino acids within the region Gly-(-3) through Thr-91. (For general sequence, see FIG. 3). Illustrative proteins are as defined in FIG. 5, but with the illustrated N-termini replacing the wild type (wt) sequence of Gly-(-3) through Thr-91.

FIG. 11 shows illustrative amino acid substitutions within the present invention.

FIGS. 12A-E show exemplary proteins containing substitutions for one or more amino acids within the region Gly-(-3) through Thr-91. (For general sequence, see FIG. 3). Illustrative proteins are as defined in FIG. 5, but with the illustrated N-termini replacing the wild type (wt) sequence of Gly-(-3) through Thr-91.

FIGS. 13A-C show illustrative compounds with multiple N-terminal substitutions with Asn-117 replaced with Gln and Arg-275 replaced with Thr.

FIG. 14 shows exemplary oligonucleotides for mutagenesis.

FIG. 15 shows exemplary mutagenized cDNA fragments.

FIGS. 16A-B show methods of preparing illustrative compounds within the present invention.

Modifications at the N-terminus

In one aspect of this invention the proteins are characterized by deletion of 1-94 amino acids within the peptide region spanning Gly-(-3) or Ser-1 through Thr-91, relative to native human t-PA. In one embodiment, for example, Cys-51 through Asp-87 of native t-PA are deleted. In two other specific embodiments Cys-6 through Ser-50, and Cys-6 through Ile-86 are deleted, respectively. In other embodiments, more conservative modifications are present in the N-terminal region of the proteins. For instance, certain proteins of this invention contain one or more amino acid deletions or substitutions within one or more of the following, more discrete subregions: as shown in FIG. 1

These and other modifications within the N-terminus spanning Gly-(-3) through Thr-91 are described in greater detail hereinafter.

B. Modifications at N-linked Glycosylation Sites

The protein variants of this invention may further contain no N-linked carbohydrate moieties or may be only partially glycosylated relative to natural human t-PA. A "partially glycosylated" protein, as the phrase is used herein, means a protein which contains fewer N-linked carbohydrate moieties than does fully-glycosylated native human t-PA. This absence of glycosylation or only partial glycosylation results from amino acid substitution or deletion at one or more of the concensus N-linked glycosylation recognition sites present in the native t-PA molecule. We have found that variant proteins of this invention embodying such modification at one or more N-linked glycosylation sites retain t-PA-type thrombolytic activity with greater fibrinolytic activity in certain cases, may be more readily produced in more homogeneous form than native t-PA, and in many cases have longer in vivo half-lives than native t-PA.

N-linked glycosylation recognition sites are presently believed to comprise tripeptide sequences which are specifically recognized by the appropriate cellular glycosylation enzymes. These tripeptide sequences are either asparagine-X-threonine or asparagine-X-serine, where X is usually any amino acid. Their location within the t-PA peptide sequence is shown in FIG. 3. A variety of amino acid substitutions or deletions at one or more of the three positions of a glycosylation recognition site results in non-glycosylation at the modified sequence. By way of example, $Asn_{117}$ and $Asn_{184}$ of t-PA have both been replaced with Thr in one embodiment and with Gln in another embodiment. At least in the case of the double Gln replacement, the resultant glycoprotein ($Gln_{117}Gln_{184}$) should contain only one N-linked carbohydrate moiety (at $Asn_{448}$) rather than two or three such moieties as in the case of native t-PA. Those skilled in the art will appreciate that analogous glycoproteins having the same $Asn_{448}$ monoglycosylation may be prepared by deletion of amino acids or substitution of other amino acids at positions 117 and 184 and/or by deleting or substituting one or more amino acids at other positions within the respective glycosylation recognitions sites, e.g. at $Ser_{119}$ and $Ser_{186}$, as mentioned above and/or by substitution, or more preferably by deletion, at one or more of the "X" positions of the tripeptide sites. In another embodiment Asn at positions 117, 184 and 448 are replaced with Gln. The resultant variants should contain no N-linked carbohydrate moieties, rather than two or three such moieties as in the case of native t-PA. In other embodiments, potential glycosylation sites have been modified individually, for instance by replacing Asn, e.g. with Gln, at position 117 in one presently preferred embodiment, at position 184 in another embodiment and at position 448 in still another embodiment. This invention encompasses such non-glycosylated, monoglycoslyated, diglycosylated and triglycosylated t-PA variants.

Exemplary modifications at one or more of the three consensus N-linked glycosylation sequences, $R^1$, $R^2$ and $R^3$, as found in various embodiments of this invention are depicted in FIG. 2.

c. Modification at the Arg-275/Ile-276 Cleavage Site

In one aspect of this invention the variants are optionally modified at the proteolytic cleavage site spanning Arg-275 and Ile-276 by virtue of deletion of Arg-275 or substitution of another amino acid, preferably an amino acid other than Lys or His, for the Arg. Thr is at present an especially prefered replacement amino acid for ARg-275 in the various embodiments of this invention. Proteolytic cleavage at Arg-275 of native t-PA yields the so-called "two-chain" molecule, as is known in the art. Proteins of this invention which are characterized by modification at this cleavage site may be more readily produced in more homogeneous form than the corresponding protein without the cleavage site modification, and perhaps more importantly may possess an improved fibrinolytic profile and pharmacokinetic characteristic.

This invention thus provides a family of novel thrombolytic proteins related to human t-PA. This family comprises several genera of proteins.

In one embodiment the proteins are characterized by a peptide sequence substantially the same as the peptide sequence of human t-PA, wherein Arg-275 is deleted or is replaced by a different amino acid, preferably other than lysine or histidine, and at least one of the consensus Asn-linked glycosylation sites is deleted or is modified to other than a consensus Asn-linked glycosylation sequence. Exemplary proteins of this embodiment are depicted in Table 1 below. By "characterized by a peptide sequence substantially the same as the peptide sequence of human t-PA," as the phrase is used herein, we mean the peptide sequence of human t-PA, or a peptide sequence encoded by a DNA sequence encoding human t-PA or a DNA sequence capable of hybridizing thereto under stringent hybridization conditions. Thus the proteins of this invention include analogs of t-PA characterized by the various modifications or combinations of modifications as disclosed herein, which may also contain other variations, e.g. allelic variations or additional deletion(s), substitution(s) or insertion(s) of amino acids which still retain thrombolytic activity, so long as the DNA encoding those proteins (prior to the modification of the invention) is still capable of hybridizing to a DNA sequence encoding human t-PA under stringent conditions.

In a second embodiment the proteins are characterized by a peptide sequence substantially the same as the peptide sequence of human t-PA wherein one or more amino acids are deleted within the N-terminal region from Gly-(-3) through Thr-91 and wherein (a) one or more Asn-linked glycosylation sites are optionally deleted or otherwise modified to other than a consensus Asn-linked glycosylation site, and/or (b) Arg-275 is optionally deleted or replaced by a different amino acid, preferably other than lysine or histidine. Exemplary proteins of this embodiment are shown in FIG. 4.

This embodiment includes a subgenus of proteins wherein 1 to about 94 amino acids are deleted from the region Gly-(-3) through Thr-91 and one or more of the Asn-linked glycosylation sites are deleted or otherwise modified to other than a consensus Asn-linked glycosylation sequence as previously described. Also included is a subgenus of compounds wherein 1 to about 94 amino acids are deleted from the region Gly-(-3) through Thr-91, and Arg-275 is deleted or replaced with a different amino acid, preferably other than lysine or histidine. A further subgenus of this embodiment is characterized by a deletion of 1 to about 94 amino acids from within the region Gly-(-3) through Thr-91, deletion or modification of one or more of the Asn-linked glycosylation sites (see e.g. the table on page 6) and deletion of Arg-275 or replacement thereof with a different amino acid. Exemplary proteins of these subgenera are depicted in FIGS. 5 and 6.

This embodiment also includes a subgenus of proteins wherein the N-terminal deletion comprises a deletion of 1 to about 45 amino acids from within the region Ser-1 through Ser-50. Also included is a subgenus of proteins wherein 1 to about 45 amino acids are deleted from within the region Ser-1 through Ser-50 and one or more glycosylation sites are modified as previously described. A further subgenus comprises proteins having a deletion of 1 to about 45 amino acids from within the region Ser-1 through Ser-50, wherein Arg-275 is deleted or replaced with another amino acid. Additionally includes is a subgenus having deletion of 1 to about 45 amino acids from within the region Ser-1 through Ser-50 and wherein both of (a) one or more glycosylation sites, and (b) Arg-275, are optionally modified as previously described. Exemplary proteins of these subgenera are depicted in FIG. 7A-D, as well as in FIGS. 5 and 6.

With reference to the modified N-termini depicted in FIG. 7A-D, it should be understood that more than one amino acid may be deleted. Where multiple amino acids are deleted, they may be adjacent to one another, or separated by one or more other amino acids. In designating compounds with such N-termini we indicate the size of the deletion by "Δn" where "n" is the number of amino acids deleted. For example, N-terminus #24 wherein one amino acid is deleted as shown in FIG. 7A-B may be referred to as "N-24Δ1". Where two amino acids are deleted, e.g. S-1 and Y-2, the N-terminus is referred to as "N-24Δ2", etc. Where combinations of deletions are made, e.g. wherein S-1, Y-2 and I-5 are deleted, the N-terminus may be referred to as "N-24Δ2, N-28Δ1". As indicated in the text following FIG. 6, specific compounds are designated by a 3-part code comprising a compound number from FIG. 5 followed by a designation of N-terminus #, e.g. from FIG. 6, and then identification of the status of position 275. Compound 2-26/N-24Δ2, N-28Δ1/-thus designates the protein wherein all three glycosylation sites; R-275; S-1, Y-2 and I-5 are deleted.

This embodiment further includes a subgenus of proteins wherein 1 to about 41 amino acids are deleted from the region Cys-51 through Thr-91. Proteins of this subgenus may optionally be modified such that Arg-275 is deleted or replaced with a different amino acid, preferably other than lysine or histidine. Proteins of this subgenus may, as an alternative to or in addition to the modification at Arg-275, be modified such that (a) one or more N-linked glycosylation sites are abolished, as previously described and/or (b) one or more amino acids are deleted within the region Gly-(-3) through Ser-50. Exemplary proteins of this subgenus are similar to those depicted in FIGS. 5 and 7A-D, but contain N-termini such as those depicted in FIG. 8A-D, below.

With reference to FIGS. 8A-D above, it should be noted that several subclasses of proteins are disclosed. For example, proteins containing a deletion of 1-37 amino acids (individually, consecutively, or in combination) from Cys-51 through Asp-87 are depicted, as are proteins containing a deletion of 1-37 amino acids from Cys-51 through Arg-87 and a deletion of one or more amino acids within the region Gly-(-3) through Cys-51 (See N-76). With reference to compounds containing an N-terminus selected from N-termini N-76 through N-111 it should be understood that more than one amino acid may be deleted. For example, N-77 wherein one amino acid is deleted, as shown in FIGS. 8A-D, may be referred to as "N-77Δ1". Where six amino acids are deleted, e.g. S-52 through F-57, the N-terminus is referred to as "N-77Δ6", etc. Specific proteins are designated as described following FIGS. 5 and 7A-D. Examples wherein the three glycosylation sites and Arg-275 are deleted are shown FIG. 9A.

Illustrative compounds wherein no modifications are present at glycosylation sites, but which contain various deletions are shown FIG. 9B.

Illustrative compounds with the same deletions as above, but which are also modified at the first N-linked glycosylation site, here by replacing Asn-117 with Gln, are listed in FIG. 9C.

Illustrative compounds with the same deletions as above, but which are also modified at all three glycosylation sites, here by replacement of Asn's with Gln's, are listed in FIG. 9D.

Thus, this embodiment further includes a subgenus of proteins wherein one or more deletions of less than about 20 amino acids are present within the region Gly-(-3) through Thr-91. Proteins of this subgenus may also be modified at Arg-275 and/or at one or more of the Asn-linked glycosylation sites. Exemplary proteins of this subgenus are similar to those depicted in FIGS. 5, 6, 7A–D and 8A, D, but contain in place of the wild type N-terminus, and N-terminus such as those depicted in FIG. 10, below. Additional exemplary compounds of this subgenus are also listed above by their 3-part code designations.

In a third embodiment the proteins are characterized by a peptide sequence substantially the same as the peptide sequence of human t-PA wherein different amino acids are substituted for 1-94 of the amino acids in the region Gly-(−3) through Thr-91. This embodiment includes a subgenus of compounds characterized by replacement of one or more amino acids within the above-mentioned N-terminus and by modification at Arg-275 as previously described. Also included is a subgenus of compounds characterized by the above-mentioned replacement of one or more amino acids within the N-terminus and modification, as previously described, at one or more of the consensus Asn-linked glycosylation sites. A further subgenus of this embodiments is characterized by substitution of one or more amino acids within the N-terminus, and modifications as previously described, at both Arg-275 and at one or more of the N-Linked glycosylation sites. In one aspect of this embodiment the amino acid substitution(s) is/are within the region Gly-(−3) through Ser-50, with or without modification at Arg-275 and/or one or more of the N-linked glycosylation sites. In another aspect, the amino acid substitution(s) is/are within the region Cys-51 through Thr-91, again, with or without modification at Arg-275 and/or at one or more of the N-linked glycosylation sites. In a further aspect, one to about eleven, preferably one to about 6 amino acids are replaced within one or more of the following regions, again with or without the other above-mentioned modification(s): as shown in FIG. 1

In a further aspect of this embodiment, the substitution(s) is/are present in one or more of the following regions: R-7 through S-20, W-21 through Y-33, N-37 through Q-42, and H-44 through S-50. In an additional aspect of this embodiment, the N-terminus is modified, again, by substitution for one to about eleven, preferably one to about six, amino acids in one or more of the above defined regions, and is further modified by deletion of one to 93, preferably 1 to about 45, and more preferably 1 to about 15, amino acids.

Illustrative amino acid substitutions are shown in FIG. 11, below, and exemplary proteins are depicted in FIGS. 12 A–E. Of the replacement amino acids for R-40, A-41 and Q-42, presented in FIG. 11, S is a preferred replacement for R-40, and V and L are preferred replacements for A-41 and Q-42, respectively. It should be noted that proteins of this invention embodying the substitutions identified for R-40, A-41 and Q-42 in FIG. 11, are presently preferred, alone, or, as in other aspects and subgenera of this embodiment, in combination with other substitution(s) and/or deletions within the N-terminus, and/or modifications at R-275 and/or at at least one glycosylation site. It is contemplated that to the extent that our proteins are modified by substitution rather than deletion, our proteins retain more of the native t-PA conformation and selectively retain more of the desirable biological activities of native t-PA.

Proteins of this invention embodying amino acid substitution(s) may be designated by a 3-part code as previously described. It should be understood of course that more than one wt amino acid may be replaced. In designating compounds with such N-termini we indicate the number of substitutions by "sn" where "n" is the number of amino acids replaced, e.g. with the replacement amino acids such as (but not limited to) those depicted in FIG. 11. For example N-terminus #N-122s1 designates N-terminus 122 as depicted in FIGS. 12A–E, while N-terminus #N-122s4 designates that N-terminus wherein S-1 is replaced with G and the following three wt amino acids are replaced with other amino acids. Proteins of this embodiment containing multiple amino acid substitutions may be designated by a string of N-terminus designations indicating specific replacements, as shown in FIGS. 13 A–C.

One subgenus of particular interest is characterized by replacement of one or more of Y-67 through S-69, with optional deletion of, and/or substitution for, one or more amino acids from Gly-(-3) through L-66, with or without modification as described above at one or more glycosylation sites and/or at Arg-275.

In one aspect of the invention the proteins contain at least one so-called "complex carbohydrate" sugar moiety characteristic of mammalian glycoproteins. As exemplified in greater detail below, such "complex carbohydrate" glycoproteins may be produced by expression of a DNA molecule encoding the desired polypeptide sequence in mammalian host cells. Suitable mammalian host cells and methods for transformation, culture, amplification, screening, and product production and purification are known in the art. See e.g. Gething and Sambrook, Nature 293:620–625 (1981), or alternatively, Kaufman et al., Molecular and Cellular Biology 5 (7):1750–1759 (1985) or Howley et al., U.S. Pat. No. 4,419,446.

A further aspect of this invention involves t-PA variants as defined above in which each carbohydrate moiety is a processed form of the initial dolicol-linked oligosaccharide characteristic of insect cell-produced glycoproteins, as opposed to a "complex carbohydrate" substituent characteristic of mammalian glycoproteins, including mammalian derived t-PA. Such insect cell-type glycosylation is referred to herein as "high mannose" carbohydrate for the sake of simplicity. For the purpose of this disclosure, complex and high mannose carbohydrates are as defined in Kornfeld et al., Ann. Rev. Biochem. 54: 631–64 (1985). "High mannose" variants in accordance with this invention are characterized by a variant polypeptide backbone as described above which contains at least one occupied N-linked glycosylation site. Such variants may be produced by expression of a DNA sequence encoding the variant in insect host cells. Suitable insect host cells as well as methods and materials for transformation/transfection, insect cell culture, screening and product production and purification useful in practicing this aspect of the invention are known in the art. Glycoproteins so produced also differ from natural t-PA and from t-PA produced heretofore by recombinant engineering techniques in mammalian cells in that the variants of this aspect of the invention do not contain terminal sialic acid or galactose substituents on the carbohydrate moieties or other protein modifications characteristic of mammalian derived glycoproteins.

The proteins of this invention which contain no N-linked carbohydrate moieties may also be produced by expressing a DNA molecule encoding the desired variant, e.g. compounds 1-6 through 1-11 or FIG. 3, in mammalian, insect, yeast or bacterial host cells, with eucaryotic host cells being presently preferred. As indicated above suitable mammalian and insect host cells, and in addition, suitable yeast and bacterial host cells, as well as methods and materials for transformation/transfection, cell culture, screening and product production and purification useful in practicing this aspect of the invention are also known in the art.

Additionally, as should be clear to those of ordinary skill in this art, this invention also contemplates other t-PA variants which are characterized, instead of by amino acid deletion within the region $Gly_{-3}$ or $Ser_1$ through $Thr_{91}$, by one or more amino acid substitutions within that region, especially in the region $Arg_7$ through $Ser_{50}$, or by a combination of deletion and substitution. cDNAs encoding these compounds may be readily prepared, e.g., by methods closely analogous to the mutagenesis procedures described herein using appropriate mutagenesis oligonucleotides. The cDNAs may be optionally mutagenized at one or more of the codons for $R^1$, $R^2$ and $R^3$, and/or Arg-275, and may be inserted into expression vectors and expressed in host cells by the methods disclosed herein. It is contemplated that these proteins will share the adavantageous pharmacokinetic properties of the other compounds of this invention, and perhaps avoid undue antigenicity upon administration in pharmacuetical preparations analogous to those disclosed herein.

As should be evident from the preceding, all variants of this invention are prepared by recombinant techniques using DNA sequences encoding the analogs which may also contain fewer or no potential glycosylation sites relative to natural human t-PA and/or deletion or replacement of Arg-275. Such DNA sequences may be produced by conventional site-directed mutagenesis of DNA sequences encoding t-PA.

DNA sequences encoding t-PA have been cloned and characterized. See e.g., D. Pennica et al., *Nature* (London) 301:214(1983) and R. Kaufman et al., Mol. Cell. Biol.5(7): 1750 (1985). One clone, ATCC 39891, which encodes a thrombolytically active t-PA analog is unique in that it contains a Met residue at position 245 rather than Val. Typically, the DNA sequence encodes a leader sequence which is processed, i.e., recognized and removed by the host cell, followed by the amino acid residues of the full length protein, beginning with Gly.Ala.Arg.Ser.Tyr.Gln. . . . Depending on the media and host cell in which the DNA sequence is expressed, the protein so produced may begin with the Gly.Ala- .Arg amino terminus or be further processed such that the first three amino acid residues are proteolytically removed. In the latter case, the mature protein has an amino terminus comprising: Ser.Tyr.Gln.Leu. . . . t-PA variants having either amino terminus are thrombolytically active and are encompassed by this invention. Variants in accord with the present invention also include proteins having either $Met_{245}$ or $Val_{245}$, as well as other variants, e.g. allelic variations or other amino acid substitutions or deletions, which still retain thrombolytic activity.

This invention also encompasses compounds as described above which contain a further modification in the polypeptide domain spanning Asn-218 through Thr-220. Specifically, compounds of this embodiment are further characterized by an amino acid other than Asn or a peptide bond at position 218 and/or an amino acid other than Pro or a peptide bond at position 219 and/or an amino acid other than Ser or Thr or a peptide bond at position 220. Compounds of this embodiment thus lack the consensus N-linked glycosylation site which is typically not glycosylated in t-PA produced by melanoma-derived mammalian cells.

As mentioned above, DNA sequences encoding individual variants of this invention may be produced by conventional site-directed mutagenesis of a DNA sequence encoding human t-PA or analogs or variants thereof. Such methods of mutagenesis include the M13 system of Zoller and Smith, Nucleic Acids Res. 10:6487–6500 (1982); Methods Enzymol. 100: 468–500 (1983); and DNA 3:479–488 (1984), using single stranded DNA and the method of Morinaga et al., Bio/technology, 636–639 (Jul. 1984), using heteroduplexed DNA. Several exemplary oligonucleotides used in accordance with such methods to effect deletions in the N-terminus or to convert an asparagine residue to threonine or glutamine, for example, are shown in FIG. 14. It should be understood, of course, that DNA encoding each of the glycoproteins of this invention may be analogously produced by one skilled in the art through site-directed mutagenesis using(an) appropriately chosen oligonucleotide(s). Expression of the DNA by conventional means in a mammalian, yeast, bacterial, or insect host cell system yields the desired variant. Mammalian expression systems and the variants obtained thereby are presently preferred.

The mammalian cell expression vectors described herein may be synthesized by techniques well known to these skilled in this art. The components of the vectors such as the bacterial replicons, selection genes, enhancers, promoters, and the like may be obtained from natural sources or synthesized by known procedures. See Kaufman et al., *J. Mol Biol.*, 59:51–521 (1982); Kaufman, *Proc Natl. Acad, Sci.* 82:689–693 (1985).

Established cell lines, including transformed cell lines, are suitable as hosts. Normal diploid cells, cell strains derived from in vitro culture of primary tissue, as well as primary explants (including relatively undifferentiated cells such as hematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese hamster Ovary) cells are presently preferred. Alternatively, the vector DNA may include all or part of the bovine papilloma virus genome (Lusky et al., Cell, 36:391–401 (1984) and be carried in cell lines such as C127 mouse cells as a stable episomal element. Other usable mammalian cell lines include but are not limited to, HeLa, COS-1 monkey cells, mouse L-929 cells, 3T3 lines derived from Swiss, Balb-c or NIH mice, BHK or HaK hamster cells lines and the like.

Stable transformants then are screened for expression of the product by standard immunological or enzymatic assays. The presence of the DNA encoding the variant proteins may be detected by standard procedures such as Southern blotting. Transient expression of the DNA encoding the variants during the several days after introduction of the expression vector DNA into suitable host cells such as COS-1 monkey cells is measured without selection by activity or immunologic assay of the proteins in the culture medium.

In the case of bacterial expression, the DNA encoding the variant may be further modified to contain different codons for bacterial expression as is known in the art and preferably is operatively linked in-frame to a nucleotide sequence encoding a secretary leader polypeptide permitting bacterial expression, secretion and processing of the mature variant protein, also as is known in the art. The compounds expressed in mammalian, insect, yeast or bacterial host cells may then be recovered, purified, and/or characterized with respect to physicochemical, biochemical and/or clinical parameters, all by known methods.

These compounds have been found to bind to monoclonal antibodies directed to human t-PA, and may thus be recovered and/or purified by immunoaffinity chromatography using such antibodies. Furthermore, these compounds possess t-PA-type enzymatic activity, i.e., compounds of this invention effectively activate plasminogen in the presence of fibrin to evoke fibrinolysis, as measured in an indirect assay using the plasmin chromogenic substrate S-2251 as is known in the art.

This invention also encompasses compositions for thrombolytic therapy which comprise a therapeutically effective amount of a variant described above in admixture with a pharmaceutically acceptable parenteral carrier. Such composition can be used in the same manner as that described for human t-PA and should be useful in humans or lower animals such as dogs, cats and other mammals known to be subject to thrombotic cardiovascular problems. It is contemplated that the compositions will be used both for treating and desirably for preventing thrombotic conditions. The exact doseage and method of administration will be determined by the attending physician depending on the potency and pharmacokinetic profile of the particular compound as well as on various factors which modify the actions of drugs, for example, body weight, sex, diet, time of administration, drug combination, reaction sensitivities and severity of the particular case.

The following examples are given to illustrate embodiments of the invention. It will be understood that these examples are illustrative, and the invention is not to be considered as restricted thereto except as indicated in the appended claims.

In each of the examples involving insect cell expression, the nuclear polyhedrosis virus used was the L-1 variant of the *Autographa Californica*, and the insect cell line used was the *spodoptera frugiperda* IPLB-SF21 cell line (Vaughn, J. L. et al., In Vitro (1977) 13, 213–217). The cell and viral manipulations were as detailed in the literature (Pennock G. D., et al., supra; Miller, D. W., Safer, P., and Miller, L. K., *Genetic Engineering*, Vol. 8, pages 277–298, J. K. Setlow and A. Hollaender, eds. Plenum Press, 1986). The RF m13 vectors, mp18 and mp 11, are commercially available from New England Biolabs. However, those of ordinary skill in the art to which this invention pertains will appreciate that other viruses, strains, host cells, promoters and vectors containing the relevant cDNA, as discussed above, may also be used in the practice of each embodiment of this invention. The DNA manipulations employed are, unless specifically set forth herein, in accordance with Maniatis et al., Molecular Cloning: A Laboratory Manual (Cold Spring Harbor, N.Y. 1982).

PLASMID DERIVATIONS

Mutagenesis of cDNAs at codons for the various amino acids was conducted using an appropriate restriction fragment of the cDNA in M13 plasmids by the method of Zoller and Smith. Deletions within the cDNA were effected by loopout mutagenesis using an appropriate restriction fragment, e.g. the SacI fragment, of the cDNA either in M13 vectors or by heteroduplex loop-out in plasmid pSVPA4.

The plasmid pSVPA4 was constructed to allow the expression of t-PA glycoprotein in mammalian cells. This plasmid was made by first removing the DNA encoding the SV40 large T polypeptide from the plasmid pspLT5 (Zhu, Z. et al., 1984, J. Virology 15:170–180). This was accomplished by performing a total Xho 1 digest followed by partial Bam-Hl restriction endonuclease digestion. The SV40 large T encoding region in pspLT5 was replaced with human t-PA-encoding sequence by ligating a cohesive SalI/ BamHl t-PA encoding restriction fragment, isolated by digesting plasmid J205 (ATCC No. 39568) with Sal I and BamHl, to the parent Xhol/BamHl cut vector pspLT5 prepared as described above. Consequently, t-PA will be transcribed in this vector under the control of the SV40 late promoter when introduced into mammalian cells. This final contruct is designated pSVPA4.

Plasmid pLDSG is an amplifiable vector for the expression of t-PA in mammalian cells such as CHO cells. pLDSG contains a mouse DHFR cDNA transcription unit which utilizes the adenovirus type 2 major late promoter (MLP), the simian virus 40 (SV40) enhancer and origin of replication, the SV40 late promoter (in the same orientation as the adenovirus MLP), a gene encoding tetracyclin resistance and a cDNA encoding human t-PA (Met-245) in the proper orientation with respect to the adenovirus type 2 MLP. The preparation of pLDSG from pCVSVL2 (ATCC No. 39813) and a t-PA encoding cDNA has been described in detail as has cotransformation with, and amplification of, pLDSG in CHO cells.. Kaufman et al., Mol, and Cell. Bio. 5(7): 1750–1759 (1985).

Plasmid pWGSM is identical to pLDSG except that the cDNA insert encodes Met-245 human t-PA. pWSGM may be constructed using cDNA from plasmid J205 (ATCC No. 39568) or pIVPA/1 (ATCC No. 39891). Throughout this disclosure pWGSM and pLDSG may be used interchangeably, although as indicated previously, the former vector will produce Val-245 proteins and the latter Met-245 proteins.

pIVPA/1 (ATCC No. 39891) is a baculoviral transplacement vector containing a t-PA-encoding cDNA. pIVPA/1 and mutagenized derivatives thereof are used to insert a desired cDNA into a baculoviral genome such that the cDNA will be under the transcriptional control of the baculoviral polyhedrin promoter.

HETERODUPLEX MUTAGENESIS

The mutagenesis via heteroduplexed DNA of specific areas in the t-PA expression plasmid, pSVPA4, involves the following steps: Preparation of ampicillin sensitive pSVPA4 DNA 1. Plasmid pSVPA4 (15 ug) was linearized with PvuI to completion. This mixture was extracted with phenol/chloroform and the DNA was precipitated using two volumes of ethanol with 0.1M NaCl present.

2. The DNA was resuspended in a 21 ul of water, 1 ul dNTB solution (containing 2 mM dATP, dGTP, dTTP, dCTP), 2.5 ul 10 X nick translation buffer (0.5M Tris-Cl pH 7.5, 0.1M MgSO$_4$, 10 mM DTT, 500 ug/ml) and 0.5 ul (2 units) DNA polymerase 1-Large Fragment (New England Biolabs). This mixture was incubated at room temperature for thirty minutes and then phenol/chlorform extracted followed by ethanol precipitation as described above.

3. The precipitated DNA was resuspended to 0.2 ug/ul by the addition of 75 ul water.

Preparation of Ampicillin Resistant pSVPA4 DNA

1. Plasmid pSVPA4 (15 ug) was digested with Sac I which cuts this plasmid twice within the t-PA encoding sequence to produce two restriction fragments, a 1.4 kbp t-PA encoding restriction fragment plus the parent vector. Following restriction digestion 1 ul (28 units) of calf intestine alkaline phospatase (Boehringer Mannheim) was added then incubated at 37° C. for five minutes. The two bands were separated by loading this mixture onto a 0.7% agarose gel. The parent vector restriction fragment was excised from the gel and extracted by adsorption to silica dioxide at 4° C., which was folowed by elution in 50 mM Tris/1 mM EDTA at 37° C. for thirty minutes. The eluted DNA was adjusted to a final concentration of 0.2 ug/ul.

Heteroduplex Annealing

1. Mix 6 ul (1.2 ug) of ampicillin sensitive pSVPA4 DNA with 6 ul (1.2 ug) ampicillin resistant pSVPA4 DNA.

2. Add an equal volume (12 ul) of 0.4M NaOH. Incubate at room temperature for ten minutes.

3. Slowly add 4.5 volumes (108 ul) of 0.1M Tris-Cl pH 7.5/20 mM HCl.

4. 50 picomoles (5 ul) of phosphorylated mutagenic oligonucleotide was added to 45 ul of heteroduplex mixture.

5. This mixture was incubated at 68° C. for two hours then slowly cooled to room temperature.

Mutagenesis

1. Each mutagenesis reaction was adjusted to the following concentrations by the addition of 7 ul to the heteroduplex mixtures, 2 mM MgCl/0.2 mM ATP/60 uM dATP, dTTP,dGTP,dCTP/4 mM DTT/40 units/ml Klenow fragment of E. coli DNA polymerase I (B.R.L.), 2000 units/ml T4 DNA ligase (N.E.B.). This mixture was incubated at room temperature for 2 hours.

2. The reaction was then phenol/chloroform extracted which was followed by ethanol precipitation. The precipitated DNA was resuspended in 12 ul 50 mM Tris-Cl/1 mM EDTA. 4 ul of this was used to transform competent HB101 bacteria.

3. Ampicillin resistant colonies were screened with $1 \times 10^6$ cpm/ml of a $^{32}$p-labeled screening oligonucleotide in 5X SSC, 0.1% SDS, 5Xdenhardt's reagent, and 100 ug/ml denatured salmon sperm DNA.

4. The filters were washed with 5X SSC, 0.1% SDS at a temperature 5° below the calculated melting temperature of the oligonucleotide probe.

5. DNA was prepared from positively hybridizing clones and analyzed initially by digestion with different restriction enzymes and agarose gel electrophoresis. DNA was transferred to nitrocellulose and filters were prepared and hybridized to the screening probes in order to ensure the mutagenic oligonucleotide was introduced in to the correct fragment.

6. DNA was then retransformed into E. coli and ampicillin resistant colonies were screened for hybridization to the screening oligonucleotide.

7. Final mutations were confirmed by DNA sequencing (Sanger).

PREPARATION OF MUTAGENIZED CDNAS: M13 METHOD

The following schematic restriction map illustrates a cDNA encoding human t-PA (above) with cleavage sites indicated for specific endonucleases (indicated below):

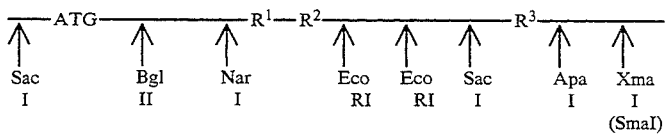

The initiation codon, ATG, and the cDNA regions encoding (a), $R^1$, $R^2$ and $R^3$ are indicated. Thus, mutagenesis at the N-terminus may be effected using the SacI fragment or the BglII/NarI fragment, for example. Mutagenesis at Arg-275 and/or at $R^1$ and/or $R^2$ may be effected using, e.g., the SacI fragment or BglII/SacI fragment. Mutagenesis at $R^3$ may be effected using, an EcoRI/XmaI or EcoRI/ApaI fragment. The choice of restriction fragment may be determined based on the convenience of using particular vectors for mutagenesis and/or for expression vector construction.

Generally, the cDNA restriction fragment to be mutagenized may be excised from the full-length cDNA present, e.g., in pWGSM, pIVPA/1 or pSVPA4, using the indicated endonuclease enzyme(s) and then mutagenized, e.g. with the oligonucleotides shown in Table 7 or other oligonucleotides designed for the desired mutagenesis.

Exemplary mutagenized cDNA fragments which may thus be prepared are shown in FIG. 15 below.

Following mutagenesis the fragment, with or without further mutagenesis, may then be excised from the M13 vector and ligated back into an expression vector containing the full-length or partial cDNA previously cleaved with the same enzyme(s) as were used for excising the mutagenized fragment from the M13 vector. By this method the full-length cDNA, mutagenized as desired, may be re-assembled using one or more mutagenized fragments as restriction fragment cassettes.

cDNAs encoding the following illustrative compounds (see FIGS. 4–7A–D may be prepared from the mutagenized fragments of FIG. 15 as shown in FIG. 16A–B.

Plasmids pIVPA or pSVPA4, in addition to utility as expression vectors, may also be used as a "depot" in the construction of cDNAs having any desired permutation of mutagenized sites. Thus, "pIVPA/Δ" or "pSVPA4/Δ", mutagenized (via M13 or heteroduplexing) plasmids containing a desired modification in the cDNA region encoding the N-terminal region may be digested with NarI (partial) and XmaI (SmaI) (total) to remove the cDNA region encoding the protein domain spanning $R^1$, $R^2$ and $R^3$. A second pIVPA or pSVPA4 plasmid mutagenized, if desired (via M13 or heteroduplexing), at any combination of Arg-275, $R^1$, $R^2$ and $R^3$-encoding regions may then be digested with NarI (total) and XmaI (SmaI) (total) and the NarI/XmaI (SmaI) fragment may then be identified, isolated and ligated into the NarI/XmaI (SmaI) digested pIVPA/Δ or pSVPA4/Δ. Such use of the NarI/XmaI (SmaI) restriction fragment cassette, for example, allows the construction of desired mutagenized cDNAs in pIVPA or pSVPA4. The mutagenized cDNA may then be transferred, e.g. as a BglII/XmaI restriction fragment cassette into BglII/XmaI-digested pWGSM for mammalian expression, if desired.

EXAMPLES

EXAMPLE 1

Preparation of $Gln_{117}$ Deletions Variants

A. Preparation of Gln-117 truncated cDNA cDNA molecules encoding the polypeptide sequence of compounds 2-1/N-21/Arg, 2-1/N-22/Arg and 2-1/N-23/Arg were prepared using the oligonucleotide-directed mutagenesis method of Zoller and Smith. Specifically, the mutagenesis vector RF M13/t-PA containing the t-PA gene was constructed from the mammalian t-PA expression plasmid pSVPA4. RF M13/t-PA was constructed by first digesting pSVPA4 to completion with the restriction endonuclease SacI. The approximately 1,436 base pair (bp) SacI fragment encodes a large portion of the polypeptide sequence of t-PA and includes the nucleotide sequences encoding the consensus N-linked glycosylation sites encompassing asparagines 117,184, and 218. This 1,436 bp (hereinafter 1.4 kbp) fragment was purified by preparative agarose gel electrophoresis.

The Sac I fragment of the t-PA cDNA, obtained as a SacI fragment, above, was ligated to a linearized double-stranded RF M13mp18 DNA vector which had been previously digested with Sac I. The ligation mixture was used to transform transformation competent bacterial JM101 cells. M13 plaques containing t-PA-derived DNA produced from transformed cells were identified and isolated by analytical DNA restriction analysis and/or plaque hybridization. Radiolabeled oligonucleotides (~17 mers, of positive polarity) derived from within the SacI restriction sites of the t-PA-encoding nucleotide sequence depicted in FIG. 3 were used as probes when filter hybridization was employed to detect viral plaques containing tPA DNA. All oligonucleotides were prepared by automated synthesis with an Applied Biosystems DNA synthesizer according to the manufacturer's instructions.

Several of the positive plaques detected by restriction or hybridization analysis were then further cloned by conventional plaque purification. Purified M13/t-PA bacteriophage obtained from the plaque purification procedure was used to infect JM101 cells. These infected cells produce cytoplasmic double-stranded "RF" M13/t-PA plasmid DNA. The infected cells also produce bacteriophage in the culture medium which contain single-stranded DNA complimentary to the 1.4 kbp SacI fragment of t-PA and to M13 DNA. Single-stranded DNA was purified from the M13/t-PA-containing phage isolated from the culture medium. This single-stranded M13/t-PA DNA was used as a template in a mutagenesis reaction according to the method of Zoller and Smith using oligonucleotide #3 of FIG. 14. This mutagenesis event changes the Asn codon to a Gln codon at position 117 of the subsequently obtained coding strand of DNA by changing the DNA sequence from "AAC" to "CAG". Following the mutagenesis reaction, the DNA was transformed into the bacterial strain JM 101. To identify mutagenized cDNA's, the transformant plaques were screened by DNA hybridization using radiolabeled oligonucleotide #4 of FIG. 14. All exemplary oligonucleotides in FIG. 14 are of positive polarity, i.e., represent portions of a coding rather than non-coding strand of DNA. All hybridization positive plaques were further purified by subsequent secondary infections of JM 101 cells with M13 phage containing mutagenized DNA.

RF M13/t-PA plasmid DNA was purified from JM 101 cells infected with purified M13 phage containing mutagenized t-PA cDNA. The RF M13/t-PA plasmid thus obtained contains the $Gln_{117}$ mutagenized Sac I restriction fragment of t-PA DNA. This mutagenized restriction fragment can then be further mutagenized, again by the method of Zoller and Smith, but using the oligonucleotides described below. The oligonucleotides described below were designed to induce a deletion ("loop out") within the cDNA region encoding the N-terminal domain.

Deletion Mutagenesis 1: Oligonucleotide #8 of FIG. 14 induced a cDNA deletion encoding Cys-6 through Ser-50, inclusive. Following this second mutagenesis reaction the DNA is transformed into JM 101 cells. To identify mutagenized cDNAs, the transformant plaques were screened as above, but using radiolabeled oligonucleotide #9 of FIG. 14. Hybridization positive plaques can be further purified by subsequent secondary infections of JM 101 cells with M13 phage containing the twice mutagenized t-PA cDNA. The cDNA prepared as described below which contains this mutagenized restriction fragment encodes compound 2-1/N-21/Arg in which Ile-5 is covalently bonded to Cys-51 by a peptide bond.

Deletion Mutagenesis 2: Oligonucleotide #10 of FIG. 14 induced a cDNA deletion encoding $Cys_6$ through $Ile_{86}$, inclusive. Following this second mutagenesis reaction the DNA is transformed into JM 101 cells. To identify mutagenized cDNAs, the transformant plaques were screened as above, but using radiolabeled oligonucleotide #11 of FIG. 14. Hybridization positive plaques can be further purified by subsequent secondary infections of JM 101 cells with M13 phage containing the twice mutagenized t-PA cDNA. The cDNA prepared as described below which contains this mutagenized fragment encodes compound 2-1/N-22/Arg in which $Ile_5$ is covalently bonded to $Asp_{87}$ by a peptide bond.

Deletion Mutagenesis 3: Oligonucleotide #12 of FIG. 14 can be used to generate a cDNA deletion encoding $Cys_{51}$ through $Asp_{87}$, inclusive. Following this second mutagenesis reaction the DNA is transformed into JM 101 cells. To identify mutagenized cDNAs, the transformant plaques were screened as above, but using radiolabeled oligonucleotide #13 of FIG. 14. Hybridization positive plaques can be further purified by subsequent secondary infections of JM 101 cells with M13 phage containing the twice mutagenized t-PA cDNA. The cDNA prepared as described below which contains this mutagenized restriction fragment encodes compound 2-/N-23/Arg in which $Ser_{50}$ is covalently bonded to $Thr_{88}$ by a peptide bond.

Each of these mutagenized restriction fragments can then be ligated back into the mammalian expression vector pSVPA4 as a Sac I cassette by methods analogous to those described in Example #3B, or prepared for insertion into the insect cell expression vector pIVPA/1 (ATCC No. 39891) as a Bgl II/Sac I cassette derived from modified RF M13/t-PA DNA.

B. Preparation of Vectors Used for Expression of High Mannose $Gln_{117}$ Deletion Variants The purified RF M13/t-PA containing the modified and truncated t-PA cDNA, prepared as described above, can be digested with the restriction endonucleases BglII and Sac I. The approximately 1.2 kbp BglII/Sac I restriction fragment was purified by conventional preparative gel electrophoresis. The BglII/Sac I fragment so obtained constitutes a mutagenized cassette which lacks a 5' and 3' portion of the DNA which encodes the amino and carboxy termini of the translated protein.

Insect expression vector pIVPA/1 (ATCC No. 39891) contains a wild type tPA cDNA insert operatively linked to a polyhedrin promoter together with baculovirus flanking DNA sequences. pIVPA/1 was digested with BglII and Sac I thereby excising a t-PA coding region spanning the N-terminus and $R^1$ and $R^2$. The BglII/Sac I cassettes containing the mutagenized, N-terminally modified t-PA cDNA fragments may each then be ligated to pIVPA/1 expression vector DNA which had been previously purified following digestion with BglII and SacI. The resulting plasmids, pIVPA/Δ FBR; $Gln_{117}$, pIVPA/Δ FBR/Δ EGF; $Gln_{117}$; pIVPA/Δ EGF, $Gln_{117}$ should contain the mutagenized cDNAs encoding compounds 2-1/N-21/Arg, 2-1/N-22/Arg and 2-1/N-23/Arg, respectively, now operatively linked to the polyhedrin promoter. The nucleotide sequence of each mutagenized cDNA insert may be confirmed by supercoil sequencing with plasmid as substrate. See e.g., E. Y. Chen et al., 1985, DNA 4(2):165-170.

B. Introduction of the Mutagenized cDNA into the Insect Virus

Each of the pIVPA plasmids containing the mutagenized cDNAs may be introduced into the insect virus by co-transfection with wild-type AcNPV in Spodoptera cells. 1 ug of purified *Autographa californica* NPV DNA and 10 ug of the desired pIVPA DNA are introduced into Spodoptera cells growing on tissue culture dishes by a calcium phosphate transfection procedure (Potter, K. N. and Miller, L. K., J. Invertebr. Path. (1980), 36 431–432). The joint introduction of these DNAs into the cells results in a double recombination event between the pIVPA plasmid (containing the mutagenized cDNAs) and the viral DNA at the regions of homology between the two; that is, the polyhedrin gene region of the progeny virus from the recombination event contains the mutagenized cDNA insert from the pIVPA plasmid.

ISOLATION OF VIRUS CONTAINING THE NUCLEOTIDE SEQUENCE ENCODING THE PROTEINS OF THIS INVENTION

The progeny virus present in the media over the transfected cells are plaqued onto a fresh monolayer of cells at several different dilutions. Plaques are assayed, and the recombinants are picked based on the PIB-minus phenotype as follows: A virus which has lost its polyhedrin gene, as would a virus containing a mutagenized cDNA will not produce PIBs. Plaques that appear PIB deficient are selected, excised and amplified on fresh cells. The supernatant over these cells is then assayed for t-PA-type enzymatic activity. Positive assay results indicate that the glycoprotein is in fact being produced.

An alternative method of virus purification via the plaque lifting protocol differs slightly from the steps described above, and is described below. Plaque the progeny virus from transfection at suitable dilution onto cell culture dishes. Prepare a nitrocellulose replica of the cell monolayer and the virus plaques. Reserve the agarose overlay from the plate as the virus source after the results of the following steps are obtained.

Probe the nitrocellulose filter with radioactive DNA fragments representative of the gene being placed into the viral chromosome. Score positives as those containing the foreign gene. Remove the hybridized probe. Re-probe the filter with radioactive DNA representative of a portion of the viral chromosome removed by substitution with the foreign DNA. One would score positives as those which still have a polyhedrin gene.

Remove the hybridized probe. Re-probe the filter with a radioactive DNA fragment which will identify viral plaques regardless of the state of the polyhedrin gene. A suitable fragment may be the EcoRI I fragment. Score these as progeny virus. Select those plaques which are positive for the foreign gene DNA probe, negative for the polyhedrin gene probe, and positive for the viral DNA probe. These are strong candidates for the desired genotype.

C. Production and Characterization of High Mannose Glycoprotein

Antibodies have been used to demostrate the presence of the variant proteins in the extracellular media of infected cells. Recombinant virus, prepared as above, is used to infect cells grown in the usual TC-100 (Gibco) nutrient salts solution but instead of the standard media supplement of 10% fetal calf serum, this is replaced with a 50% egg yolk enrichment (to 1% total volume) (Scott Biologicals). Previous experiments had demonstrated a more intact protein under these conditions. The supernatant from the infected cells is fractionated on an affinity column bearing an attached monoclonal antibody to natural human t-PA. Protein specifically retained by the column is eluted and assayed for t-PA enzymatic activity. A fixed amount of activity units of this and control t-PA preparations are separated on an acrylamide gel. This gel is then stained with a silver-based reagent to display the protein pattern. This reveals that the virus, upon infection of insect cells, leads to the extracellular production of a protein having t-PA type activity.

Radiolabeled protein is produced for further characterization by first incubating *spodoptera frugiperda* cells infected with the virus (m.o.i=1) for 48 hours. The culture plates are then rinsed with methionine-deficient media. Methionine-deficient media supplemented with $^{35}s$-methione is then added to the culture plates. The cell cultures are incubated for 4 hours. The supernatant containing the radiolabeled glycoprotein may be analyzed by SDS-PAGE (7.5%) against wild type (i.e. full-length fully glycosylated) t-PA analogously produced in insect cells and against mammalian t-PA produced e.g. by the method of R. Kaufman et al., Mol. Cell. Biol. 5(7):1750(1985)., but in the presence of tunicamycin (non-glycosylated). The partially glycosylated truncated proteins produced in Example 1 should have an increased gel mobility relative to the fully-glycosylated analog and to the non-glycosylated full-length analog.

EXAMPLE 2

Preparation of Other Proteins of this Invention

A. Preparation of other cDNA's The mutagenesis methods of Example 1 can be used with other conventionally prepared synthetic oligonucleotides which modify the original t-PA DNA sequence to produce proteins modified at the N-terminal region and/or optionally modified at N-linked glycosylation sites and/or at Arg-275 with the appropriate codon change(s) described previously. See, e.g. "Preparation of Mutagenized cDNAs: M13 Method" and Routes (a)–(h), supra.

For example, cDNA encoding Compounds D-6, D-1 and D-3 may be prepared using the SacI restriction fragment in M13/t-PA and mutagenizing with oligonucleotides #8, 10 and 12 respectively, but not with oligonucleotide #3. Arg-275 may be deleted or replaced, eg with Thr, using oligo's 14 or 15, respectively. Vector construction, transfection and expression may be carried out as in Example 1 for insect cells or as described below in Example 3 for mammalian cells.

Single-stranded DNA generated from the M13 mutagenesis vector (RF M13/t-PA), prepared as in Example 1, can also be used as a template to mutagenize, in a site specific manner, at Arg-275 and/or at glycosylation site(s) $R^1$ or $R^2$ or both. The region encoding the consensus tripeptide which encompasses $Asn_{218}$ may be similarly mutagenized. To prepare multiple modifications of the protein at these sites an iterative process may be used. For example, following the identification and the purification of M13 phage containing a modified $R^1$ site, single-stranded DNA containing this modified site can be purified from phage and used as template to initiate a second round of mutagenesis within the $R^2$ site and/or at Arg-275. This process can be repeated until all desired modifications are obtained. Thus, cDNA encoding Compounds 2-2/N-23/Arg, 2-2/N-21/Arg and 2-2/N-22/Arg may be prepared by the method of Example 1 but substituting mutagenesis oligonucleotide #5 for oligonucleotide #3 and screening oligonucleotide #6 for oligonucleotide #4. cDNA encoding Compounds 2-6/N-21/Arg, 2-6/N-22/Arg and 2-6/N-23/Arg may be prepared by twice mutagenizing the SacI fragment as described in Example 1 and addition mutagenizing and screening with oligonucleotides #5 and #6. Vector construction, transfection and expression are carried out as in Example 1 for insect cells or as described below for mammalian cells. See Routes (a)–(h), supra.

The RF M13/t-PA mutagenesis vector does not contain DNA sequence encoding $R^3$, the N-linked glycosylation site of t-PA most proximal to the carboxy-terminus of the protein. Therefore in order to make DNA modifications at that site, a new M13/t-PA mutagenesis RF vector called M13/t-PA:RI-Xma I was made. This vector was constructed by digesting the M13 vector M13mp11 to completion with EcoRI and Xma I. The RI/XmaI digested M13 vector was ligated to a purified EcoRI/Xma I t-PA restriction fragment (approximately 439 bp, hereinafter 0.4 kbp) encoding a polypeptide region encompassing glycosylation site $R^3$. This 0.4 kbp restriction fragment was purified following digestion of the plasmid pWGSM with EcoRI and Xma I. The mammalian expression plasmid pWGSM, encoding the t-PA gene, is identical within the 439 bp EcoRI/Xma I fragment to the plasmid pLDSG described by Kaufman et al., Mol. Cell Biol. 5:1750–1759 (1985).

The ligation mixture was used to transform competent bacterial JM 101 cells. Several plaques were picked and analyzed for the presence of the 0.4 kbp t-PA EcoRI/XmaI fragment by standard DNA restriction fragment analysis. Double-stranded RF M13 DNA was purified from cells containing the 0.4 kbp t-PA fragment. This DNA was designated RF M13/t-PA:RI-Xma I mutagenesis vector. As previously indicated in Example 1A this vector, when transformed into competent JM101 cells, can be used to make M13/t-PA:RI-XmaI phage from which single-stranded M13/t-PA:RI-XmaI DNA can be purified. This single-stranded DNA can be used as template in the site-directed mutagenesis reaction to modify the t-PA DNA at the N-linked glycosylation site $R^3$.

Modified $R^3$ coding sequences can be used to replace the wild-type $R^3$ sequences present in either modified pIVPA/1 as prepared in Example 1 (truncated and/or modified at $R^1$ and/or $R^2$) or wild-type pIVPA/1 plasmid DNA. This can be accomplished by first performing a total Sac I/Apa I digestion of the $R^3$ modified M13/t-PA:RI/XmaI mutagenesis plasmid vector, and isolating the $R^3$ modified 165 base pair t-PA restriction fragment so produced. The insect expression vector pIVPA/1 or pIVPA/1 plasmid DNA modified, e.g. as in Example 1, can similarly be totally digested with Sac I and Apa I to excise the 165 bp wild-type t-PA restriction fragment encoding the unmodified $R^3$ site. Ligation of the purified insect expression vector lacking the 165 bp fragment to the modified $R^3$ 165 bp fragment produces a new insect expression vector. Expression of the vector produces a truncated protein modified at the $R^3$ site, as well as at any or all of the other consensus N-linked glycosylation sites present in natural t-PA and/or at Arg-275.

The pIVPA plasmid containing the modified cDNA may also be used to generate the BglII/ApaI fragment of the modified t-PA cDNA which spans the deletion region in the N-terminal domain as well as the region encoding $R^1$, $R^2$ and $R^3$ or the NarI/XmaI fragment which spans $R^1$, $R^2$ and $R^3$. Either of those fragments may be inserted into mammalian expression vectors such as pSVPA4 or pWGSM as described in Example 3.

EXAMPLE 3

Preparation of Compounds D-6, D-1 and D-3 in Mammalian Cells

A. Preparation of cDNA.

cDNA molecules encoding the polypeptide sequences of compounds D-6, D-1 and D-3 were prepared using mutagenesis oligonucleotides #8, 10, and 12, respectively, and the SacI fragment of the t-PA cDNA as template by the M13 method of Example 1 or heteroduplex mutagenesis (Moranaga Heteroduplex Mutagenesis protocol; both, supra). Mutants selected by DNA hybridization using screening oligonucleotides 9, 11 and 13 respectively were confirmed by DNA sequence analysis to be correct in the modified DNA sequence.

B. Modified t-PA Vector Preparation

Each modified cDNA prepared in Example 1A (Δ, $Gln_{117}$) or 3A (Δ) was first removed from the M13 mutagenesis vector RF M13/t-PA by total digestion of the vector with SacI. The approximately 1.4 kbp restriction fragment of each mutagenized cDNA was purified by gel electrophoresis and then ligated into pSVPA4 as follows. First, pSVPA4 was digested with SacI to remove the wild type t-PA 1.4 kbp restriction fragment. The remaining portion of the SacI digested pSVPA4 was then ligated to the 1.4 bkp restriction fragment of the mutagenized cDNA. This ligation event can produce two orientations of the inserted fragment. The appropriate orientation in each case may be identified using EcoRI and PvuII as the enzymes in conventional analytical restriction enzyme analysis. This replacement allows the Sac I fragment to be used as a cassette fragment between the RF M13/t-PA mutagenesis vector and the pSVPA4 mammalian expression vector. Modified M13 SacI fragments (truncated and optionally modified at $R^1$ and/or $R^2$) may be inserted into SacI-digested pSVPA4 DNA which has been previously, or is subsequently, modified at $R^3$ if desired. Alternatively, DNA previously modified at $R^1$, $R^2$ and/or $R^3$ can be excised from vectors such as pIVPA or pSVPA4 as a NarI/ApaI or NarI/XmaI fragment. The fragment so obtained may then be inserted into vectors such as pSVPA4 or pWGSM previously digested with NarI (partial) and ApaI or XmaI (total). By this method any combination of N-terminal deletion and/or substitution and/or glycosylation site mutagenesis and/or Arg-275 mutagenesis may be achieved.

c. Transfection of COS (SV40 transformed African Green Monkey Kidney) Cells

COS-1 cells (ATCC CRL 1650) were transfected by the method of Lopata, M. A. et al., Nucl. Acids Res. 12:5707–5717 (1984) with the vectors prepared in Example 3B, i.e., modified pSVPA4. Serum containing medium was replaced with serum-free medium 24 hours after the transfection and conditioned medium was assayed for both the presence of plasminogen activating activity, using the chromogenic substrate S-2251, or the presence of t-PA antigen by an ELISA assay, 48 and 72 hours post-transfection.

D. Viral Propagation in CV1 (African Green Monkey Kidney) Cells.

Modified complex carbohydrate protein can be produced by infecting CV1 cells (ATCC CLL 70) with SV40 viral stocks propagated as described by Gething and Sambrook (Nature 293:620–625, 1981). This has been carried out by first totally digesting modified pSVPA4 with the restriction endonuclease BamHI to remove the bacterial shuttle vector pXf3 from the SV40 viral DNA. Before transfecting this DNA into CV1 cells, along with the helper virus SV40-rINS-pBR322 DNA (described below), the Bam HI linearized SV40/t-PA DNA is circularized by ligation at dilute DNA concentrations (1 ug/ml). This process was repeated with the insulin containing SV40 vector SV40-rINS-pBR322 (Horowitz, M. et al., 1982, Eukaryotic Viral Vectors, pp. 47–53, Cold Spring Harbor Laboratory). The bacterial shuttle vector pBR322 in SV40-rINS-pBR322 was removed by a total EcoRI digestion. The linearized insulin/SV40 viral DNA was then circularized by ligation at a DNA concentration of 1 ug/ml. It is necessary to transfect CV-1 cells with circular ligated pSVPA4 and SV40-rINS DNAs, at equimolar amounts in order to generate viral stocks. SV40rINS is used to provide "late" SV40 proteins while pSVPA4 provides the "early" SV40 proteins necessary for virus DNA production while also encoding the proteins of this invention. Consequently when cells are transfected with both these DNA's as described by Gething and Sambrook, SV40 virus is produced which contains DNA from either viral vectors. Subsequent infection of CV1 cells with amplified virus has produced protein with t-PA-type activity which can be assayed 72 hours post-infection as described in Example 3C.

EXAMPLE 4

Preparation of Other Proteins cDNAs encoding various proteins of this invention have been prepared by the methods of Examples 1, 2 and 3. The BglII/XmaI restriction fragment cassette may then be excised from either the pIVPA or pSVPA4 vector containing the cDNA encoding the truncated protein with or without modification at one or more glycosylation sites. The excised BglII/XmaI fragment may then be ligated into BglII/XmaI-cut pSVPA4 or pWGSM for introduction into mammalian cells. Expression of such cDNAs in mammalian host cells, e.g. by the method of Example 3 or by the method of Kaufman et al., supra, (CHO host cells) or by the method of Howley et al., U.S. Pat. No. 4,419,446 (1983) (BPV expression systems) yields the corresponding mammalian-derived truncated proteins. Thus, cDNAs encoding compounds 2-1/N-21/Arg ($\Delta$ FBR, Gln$_{117}$) and 2-1/N-22/Arg ($\Delta$ FBR/EGF, Gln$_{117}$) were prepared and inserted into pSVPA4 as described above. cDNA encoding compound 2-1/N-23/Arg ($\Delta$ EGF, Gln$_{117}$) was prepared using mutagenesis oligonucleotide #12 and screening oligonucleotide #13 (Table 7) but by the heteroduplex method described above, with pSVPA4 previously mutagenized at position 117 (as above) as template. Similarly, cDNAs encoding Compounds D-1 ($\Delta$ FBR) and D-3 ($\Delta$ EGF/FBR) were prepared by M13 mutagenesis, as described above, and inserted as the SacI fragment into SacI-digested pSVPA4. cDNA encoding Compound D-6 ($\Delta$ EGF) was prepared by the heteroduplex method, described above, using pSVPA4 as template and mutagenesis oligonucleotide #12, and screening with oligonucleotide #13.

To prepare the cDNAs encoding the proteins for amplification and expression in mammalian cells, cDNA contained in pSVPA4 or pIVPA is excised as a BglII/XmaI fragment and ligated into purified, BglII/XmaI-digested pWGSM. In each case the resulting pWGSM vector is introduced into CHO cells and amplified by the method of Kaufman, supra. The transformed and amplified CHO cells produce compounds D-6, D-1, D-3, 2-1/N-23/Arg, 2-1/N-21/Arg and 2-1/N-22/Arg respectively, which were detected in the culture medium by human t-PA specific antibodies. The compounds may then be recovered and purified by immunoaffinity chromatography.

EXAMPLE 5

Example 4 may be repeated using cDNA encoding the proteins modified within the N-terminus and/or at R-275 with or without modification at $R^1$, $R^2$, and/or $R^3$ to produce the desired protein in CHO cells. Mutagenized cDNAs may be prepared as described above. Thus, cDNAs encoding Compounds 2-7/N-23/Arg, 2-7/N-21/Arg and 2-7/N-22/Arg are prepared in pIVPA as described in Example 2. The cDNAs may then be excised as the BglII/XmaI fragment and ligated into purified, BglII/XmaI-digested pWGSM, and the resultant vector transformed and amplified in CHO cells as in Example 4 to produce compounds 2-7/N-23/Arg, 2-7/N-21/Arg and 2-7/N-22/Arg.

What is claimed is:

1. A DNA molecule encoding a thrombolytic protein consisting of the peptide sequence of human t-PA, wherein:
   (a) DNA sequence encoding Cys-6 through Ile-86 is deleted, and
   (b) DNA sequence encoding the N-linked glycosylation sites at positions 117–119, 184–186, and 448–450 are modified such that Asn-117, Asn 184 and Asn 448 are replaced with Gln.

2. The DNA molecule of claim 1, wherein the DNA sequence encoding the amino acid at position 245, encodes either Met or Val.